(12) United States Patent
Bozich et al.

(10) Patent No.: US 7,914,350 B1
(45) Date of Patent: Mar. 29, 2011

(54) APPARATUS, SYSTEM, AND METHOD FOR CREATING AN ELECTRICAL CONNECTION TO A TOOL

(75) Inventors: John M. Bozich, Kennewick, WA (US); John Cadwell, Kennewick, WA (US)

(73) Assignee: Cadwell Labs, Kennewick, WA (US)

( * ) Notice: Subject to any disclaimer, the term of this patent is extended or adjusted under 35 U.S.C. 154(b) by 0 days.

(21) Appl. No.: 12/758,931

(22) Filed: Apr. 13, 2010

(51) Int. Cl.
*H01R 4/48* (2006.01)

(52) U.S. Cl. ........ 439/822; 439/506; 439/759; 439/829; 439/909

(58) Field of Classification Search .......... 439/506, 439/759, 822, 829, 909
See application file for complete search history.

(56) References Cited

U.S. PATENT DOCUMENTS

| | | | |
|---|---|---|---|
| 1,477,527 A | 12/1923 | Raettig | |
| 3,188,605 A * | 6/1965 | Slenker | 439/829 |
| 3,617,616 A | 11/1971 | O'Loughlin | |
| 3,646,500 A | 2/1972 | Wessely | |
| 3,733,574 A | 5/1973 | Scoville et al. | |
| 4,444,187 A | 4/1984 | Perlin | |
| 4,934,957 A * | 6/1990 | Bellusci | 439/829 |
| 4,998,796 A | 3/1991 | Bonanni et al. | |
| 5,514,005 A | 5/1996 | Jaycox et al. | |
| 5,928,030 A | 7/1999 | Daoud et al. | |
| 6,568,961 B1 | 5/2003 | Liburdi | |
| 6,623,500 B1 | 9/2003 | Cook et al. | |
| 6,638,101 B1 * | 10/2003 | Botelho | 439/829 |
| 2006/0173383 A1 | 8/2006 | Esteve et al. | |
| 2009/0197476 A1 | 8/2009 | Wallace | |
| 2009/0221153 A1 | 9/2009 | Santangelo et al. | |

* cited by examiner

*Primary Examiner* — Tho D Ta
(74) *Attorney, Agent, or Firm* — Kunzler Needham Massey & Thorpe

(57) ABSTRACT

An apparatus, system, and method are disclosed for creating an electrical connection with an electrically conductive element. The apparatus includes a first contact element having an engagement surface for engaging a first side of the electrically conductive element and a second contact element positioned opposite the first contact element includes an opposing engagement surface for engaging a second side of the electrically conductive element. The first contact element is slideable past the second contact element to form a scissor-like jaw. A valley formed in at least one of the engagement surface and the opposing engagement surface of the first and second contact elements creates a stage. At least one of the first and the second contact elements are made of an electrically conductive material that conducts an electrical current between the electrically conductive element and at least one of the first and second contact elements.

19 Claims, 9 Drawing Sheets

APPARATUS, SYSTEM, AND METHOD FOR CREATING AN ELECTRICAL CONNECTION TO A TOOL

FIELD OF THE INVENTION

This invention relates to electrical clips that engage an electrically conductive element to create an electrical connection between the electrical clip and the electrically conductive element and more particularly relates to electrical clips that allow a conductive shaft of an electrically conductive element to rotate while maintaining an electrical connection to the electrically conductive element.

BACKGROUND

Description of the Related Art

Electrical connectors of various types are used for various purposes. One such purpose is the application of an electrical current to a surgical tool. Often, an electrical clip is connected via an electrical cord to a power source. This allows a surgeon or other medical staff to determine if he or she is working to close to a nerve. However, because surgical tools are often used to perform very delicate and accurate steps, the attached electrical clip and corresponding cord may make it difficult to use the tool according to its designed functions. For example, the tool may be rotated during its normal use. This can cause difficulties in using the tool when an electrical clip is attached because the cord may wrap around the tool. Similar difficulties may arise with any tool that is designed to both deliver an electrical current and perform additional operations or functions which require the tool to be rotated or manipulated.

SUMMARY

From the foregoing discussion, it should be apparent that a need exists for an apparatus, system, and method that allow a user to manipulate a tool while maintaining an electrical connection to the tool. Beneficially, such an apparatus, system, and method would create and maintain an electrical connection with the tool even when the tool is rotated.

The present invention has been developed in response to the present state of the art, and in particular, in response to the problems and needs in the art that have not yet been fully solved by currently available electrical connectors. Accordingly, the present invention has been developed to provide an apparatus, system, and method for creating an electrical connection with an electrically conductive element that overcome many or all of the above-discussed shortcomings in the art.

The apparatus to create an electrical connection with an electrically conductive element includes a first contact element, a second contact element, and at least one stage formed in a scissor-like jaw created by the first contact element and the second contact element.

In certain embodiments the first contact element includes an engagement surface for engaging a first side of the electrically conductive element. The second contact element includes an opposing engagement surface for engaging a second side of the electrically conductive element. The second contact element is positioned opposite the first contact element and the first contact element is slideable past the second contact element to form a scissor-like jaw.

At least one stage is formed in the scissor-like jaw. The stage is a valley formed in at least one of the engagement surface of the first contact element and the opposing engagement surface of the second contact element. At least one of the first contact element and the second contact element are made of an electrically conductive material that conducts an electrical current between the electrically conductive element and at least one of the first contact element and the second contact element.

In certain embodiments at least one of the first contact element and the second contact element is resiliently biased to position the scissor-like jaw in the closed position. The first contact element overlaps the second contact element when the scissor-like jaw is positioned in the closed position. In some embodiments at least one of the first contact element and the second contact element are made of a material having a structural resiliency sufficient to resiliently bias the scissor-like jaw in the closed position. In one embodiment at least one of the first contact element and the second contact element are a wireform having a structural resiliency sufficient to resiliently bias the scissor-like jaw in the closed position.

In another embodiment the apparatus includes a biasing element coupled to at least one of the first contact element and the second contact element. The biasing element resiliently biases the scissor-like jaw in the closed position.

The apparatus, in one embodiment, includes a housing that engages at least one of the first contact element and the second contact element to bias the scissor-like jaw in a closed position. The housing may include at least one prong rigidly extending from a substantially rigid support base with the first contact element and the second contact element including a receiving end and a recessed end. At least one of the first contact element and the second contact element is engaged with the housing at one or more of the receiving end and the recessed end of the first and/or second contact element. The housing provides a substantially rigid support structure against which at least one of the first contact element and the second contact element apply a biasing force to bias the scissor-like jaw in the closed position.

In one embodiment at least one of the first contact element and the second contact element include an angled section at a receiving end of the scissor-like jaw. The angled section deflects to receive the electrically conductive element.

In certain embodiments the apparatus includes a number of stages with each stage being a different sized stage. Each stage may be a successively smaller stage deeper within the scissor-like jaw in one embodiment. The electrically conductive element may be selectively placed in a different stage based on at least one of a size of the electrically conductive element and a desired amount of tension between the electrically conductive element and the first contact element and the second contact element.

In an exemplary embodiment, the electrically conductive element is a shaft of a tool and an electrical connection is maintained when the shaft of the tool is rotated relative to the scissor-like jaw.

The apparatus may also include, in certain embodiments, an electrical connector coupled to at least one of the first contact element and the second contact element. In another embodiment the apparatus includes a feedback indicator that provides feedback to a user in response to a feedback signal from the electrically conductive element.

In certain embodiments the apparatus may also include one or more of a resistor, a potentiometer, and a switch. The resistor, potentiometer, and/or switch may control a level of electric current between an electrical source and at least one of the one of the first contact element and the second contact element.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 2D is a cutaway side view of one embodiment of the apparatus of

FIG. 2A prior to insertion of an electrically conductive element into the scissor-like jaw;

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1A:
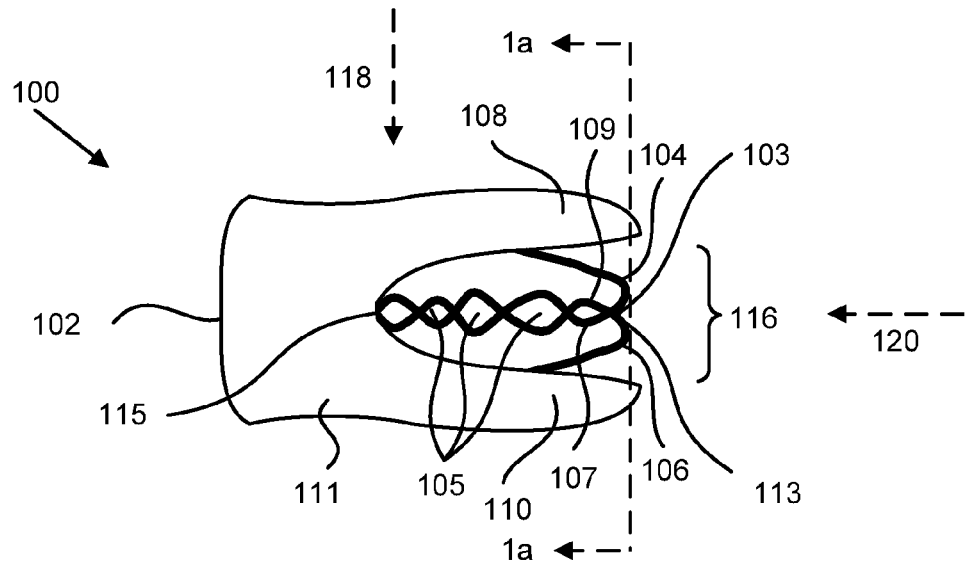
FIG. 1A is a side view illustrating one embodiment of an apparatus for creating an electrical connection with an electrically conductive element.

FIG. 1A is a side view of one exemplary embodiment of an apparatus 100 for creating an electrical connection to a conductive shaft. The apparatus 100 includes a housing 102, a first contact element 104 and a second contact element 106.

The first contact element 104 includes an engagement surface 107 for engaging a first side of an electrically conductive element (not shown in FIG. 1A). The second contact element 106 has an opposing engagement surface 109 for engaging a second side of the electrically conductive element (not shown in FIG. 1A). The second contact element 106 is positioned opposite the first contact element 104 and is slideable past the second contact element 104 to form a scissor-like jaw 103.

At least one stage 105 is formed in the scissor-like jaw 103 to retain the electrically conductive element (not shown in FIG. 1A) within the scissor-like jaw 103. The stages 105 include a valley formed in the engagement surface 107 of the first contact element 104 and/or a valley formed in the opposing engagement surface 109 of the second contact element 106. In certain embodiments only one of the engagement surface 107 of the first contact element 104 or the opposing engagement surface 109 of the second contact element 106 include valleys to form the stages 105. One of skill in the art will recognize that in certain embodiments the scissor-like jaw 103 may include a single stage 105 to retain the electrically conductive element (not shown in FIG. 1A).

Where the scissor-like jaw includes multiple stages 105, each stage may be sized differently to accommodate different sized electrically conductive elements (not shown in FIG. 1A). For example, in one embodiment the stage 105 closest the receiving ends 113 of the first and second contact elements 104, 106 may be sized to receive a relatively large electrically conductive element (not shown in FIG. 1A). Each successive stage 105 may be successively smaller to receive successively smaller electrically conductive elements (not shown in FIG. 1A) deeper within the scissor-like jaw 103. In certain embodiments the successively smaller stages 105 may receive the same sized electrically conductive element (not shown in FIG. 1A) and may place an increased tension on the electrically conductive element (not shown in FIG. 1A) as the electrically conductive element (not shown in FIG. 1A) is positioned deeper within the scissor-like jaw 103.

In other embodiments, the arrangement of the sizes of the stages 105 may be reversed such that the stage 105 closest the receiving ends 113 of the first and second contact elements 104, 106 is the smallest with the stages 105 progressively increasing in size deeper within the scissor-like jaw 103. In either case, the electrically conductive element (not shown in FIG. 1A) may be selectively positioned in a different stage 105 based on the size of the electrically conductive element (not shown in FIG. 1A), the desired amount of tension between the electrically conductive element (not shown in FIG. 1A) and the first contact element 104 and the second contact element 106, or both.

In certain embodiments both the first contact element 104 and the second contact element 106 are made of an electrically conductive material that conducts an electrical current between the electrically conductive element and the first contact element 104 and the second contact element 106. In other embodiments only one of the first contact element 104 or the second contact element 106 are made of an electrically conductive material.

The embodiment illustrated in FIG. 1A depicts both the engagement surface 107 of the first contact element 104 and the opposing engagement surface 109 of the second contact element 106 as including multiple valleys forming multiple stages 105. The first contact element 104 and second contact element 106 are opposing contact elements that form a scissor-like jaw 103 to engage the conductive shaft (not shown in FIG. 1A). For example, a conductive shaft of the electrically conductive element (not shown in FIG. 1A) may be inserted into the scissor-like jaw 103 with the first contact element 104 above and the second contact element 106 below.

When the scissor-like jaw 103 is in a closed position, as depicted, the first contact element 104 overlaps vertically with the second contact element 106. In certain embodiments the first contact element 104 and the second contact element 106 are resiliently biased to position the scissor-like jaw 103 in the closed position. In another embodiment only one of the first contact element 104 or the second contact element 106 is resiliently biased to position the scissor-like jaw 103 in the closed position. One of skill in the art will recognize that in certain embodiments one of the first contact element 104 or the second contact element 106 may be rigidly fixed in position and the other contact element (104 or 106) may be resiliently biased to position the scissor-like jaw 103 in the closed position. Further operation of the scissor-like jaw 103 will be discussed in relation to later figures.

The housing 102 provides a substantially rigid support structure against which at least one of the first contact element 104 and/or the second contact element 106 apply a biasing force to bias the scissor-like jaw 103 in the closed position. In one embodiment the housing 102 may engage at least one of the first contact element 104 and/or the second contact element 106 to bias the scissor-like jaw 103 in the closed position. In another embodiment the housing 102 includes prongs 108 and 110 rigidly extending from a substantially rigid support base 111. The first contact element 104 and the second contact element 106 include a receiving end 113 and a recessed end 115 which are engaged with the housing 102 at the receiving end 113 and/or the recessed end 115 of the first contact element 104 and the second contact element 106.

The receiving end 113 of the first contact element 104 and/or the receiving end 113 of second contact element 106 may engage the prongs 108 or 110 of the housing 102 and the recessed end 115 of the first contact element 104 and/or the recessed end 115 of the second contact element 106 may be free floating. In another embodiment the recessed end 115 of the first contact element 104 and/or the recessed end 115 of the second contact element 106 may engage the support base 111 and the receiving end 113 of the first contact element 104 and/or the receiving end 113 of second contact element 106 may be free floating. In yet another embodiment both the recessed ends 115 of the first and second contact element 104, 106 and the receiving ends 113 of the first and second contact element 104, 106 may be engaged with the housing 102. One of skill in the art will recognize that in certain embodiments one of the first contact element 104 or the second contact element 106 may be rigidly coupled to the housing and the other contact element (104 or 106) may engage the housing 102 to bias the scissor-like jaw 103 in the closed position.

Figure 1B:
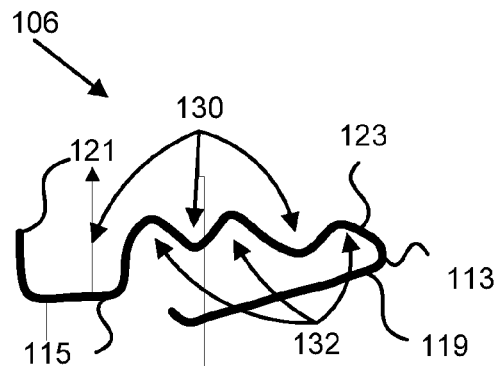
FIG. 1B is a side view of one embodiment of the second contact element of FIG. 1A absent the housing of FIG. 1A.

FIG. 1B depicts the second contact element 106 while omitting other portions of the apparatus 100. In certain embodiments the second contact element 106 comprises a plurality of valleys 130 and peaks 132 that cooperate with the first contact element 104 to form stages 105 in the scissor-like jaw 103. The valleys 130 comprise portions of the second contact element 106 that are concave towards the center of the scissor-like jaw 103. In other words, the valleys 130 are concave away from a conductive shaft of an electrically conductive element (not shown in FIG. 1B) inserted into the scissor-like jaw 103, allowing the shaft to rest in the valley 130. In the depiction of FIG. 1B the valleys 130 are depicted such that they are in a concave downward orientation. A conductive shaft of an electrically conductive element (not shown in FIG. 1B) inserted into the scissor-like jaw 103 will be positioned above the second contact element 106 to rest in one of the valleys 130. The peaks 132 comprise portions of the second contact element 106 that are convex towards the center of the scissor-like jaw 103. In other words, the peaks 132 would be convex towards a conductive shaft inserted into the scissor-like jaw 103. In the depiction of FIG. 1B the peaks 132 are depicted such that they are in a convex upward orientation.

In certain embodiments the receiving end 113 of the second contact element 106 includes a receiving end leveraging structure 119 that extends from the receiving end 113 to engage the receiving end 113 with the prong 110 of the housing 102. The recessed end 115 may also include a recessed end leveraging structure 121 that extends from the recessed end 115 to engage the receiving end 115 with the support base 111 of the housing 102. As discussed above, in certain embodiments only one of the receiving end 113 or the recessed end 115 is engaged with the housing 102. In such embodiments the receiving end leveraging structure 119 or the recessed end leveraging structure 121 may be omitted.

The second contact element 106 may be made of a material having a structural resiliency sufficient to resiliently bias the scissor-like jaw 103 in the closed position when the second contact element 106 is engaged with the housing 102. For example, in certain embodiments the second contact element 106 may be a wireform, as depicted in FIG. 1B. The material of the wireform may be selected such that the wireform has a structural resiliency sufficient to resiliently bias the scissor-like jaw 103 in the closed position. One of skill in the art will recognize that in other embodiments the second contact element 106 may be a thin sheet of metal or other electrically conductive material having a structural resiliency sufficient to bias the scissor-like jaw 103 in the closed position.

Figure 1C:
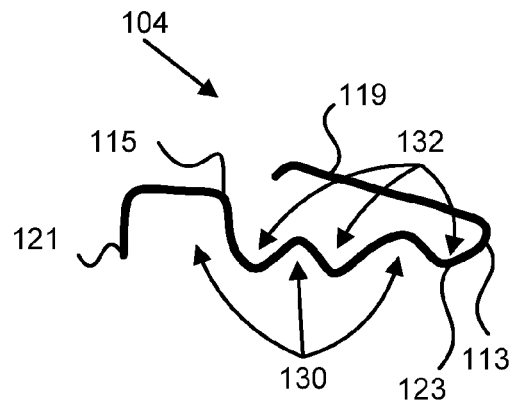
FIG. 1C is a side view of one embodiment of the first contact element of FIG. 1A absent the housing of FIG. 1A.

FIG. 1C depicts the first contact element 104 while omitting other portions of the apparatus 100. In the depicted embodiment, the first contact element 104 also comprises a plurality of valleys 130 and peaks 132. The valleys 130 comprise portions of the first contact 104 that are concave towards the center of the scissor-like jaw 103. In other words, the valleys 130 are concave away from a conductive shaft of an electrically conductive element (not shown in FIG. 1C) inserted into the jaw 103. In the depiction of FIG. 1C the valleys 130 are depicted such that they are in a concave upward orientation. A conductive shaft of an electrically conductive element (not shown in FIG. 1C) inserted into the scissor-like jaw 103 will be positioned below the second contact element 106 and rest in a valley 130. The peaks 132 include portions of the first contact element 104 that are convex towards the center of the scissor-like jaw 103. In other words, the peaks 132 would be convex towards a conductive shaft inserted into the scissor-like jaw 103. In the depiction of FIG. 1C the peaks 132 are depicted such that they are in a convex downward orientation.

In certain embodiments the receiving end 113 of the first contact element 104 also includes a receiving end leveraging structure 119 that extends from the receiving end 113 to engage the receiving end 113 with the prong 108 of the housing 102. The recessed end 115 may also include a recessed end leveraging structure 121 that extends from the recessed end 115 to engage the receiving end 115 with the support base 111 of the housing 102. As discussed above, in certain embodiments only one of the receiving end 113 or the recessed end 115 is engaged with the housing 102. In such embodiments the receiving end leveraging structure 119 or the recessed end leveraging structure 121 may be omitted.

The first contact element 104 may be made of a material having a structural resiliency sufficient to resiliently bias the scissor-like jaw 103 in the closed position when the first contact element 104 is engaged with the housing 102. For example, in certain embodiments the first contact element 104 may be a wireform, as depicted in FIG. 1B. The material of the wireform may be selected such that the wireform has a structural resiliency sufficient to resiliently bias the scissor-like jaw 103 in the closed position. One of skill in the art will recognize that in other embodiments the first contact element 104 may be a sheet of metal or other electrically conductive material having a structural resiliency sufficient to bias the scissor-like jaw 103 in the closed position. In certain embodiments both the first contact element 104 and the second contact element 106 may be made of a material having having a structural resiliency sufficient to resiliently bias the scissor-like jaw 103 in the closed position.

Also more clearly illustrated in FIGS. 1B and 1C are the shapes of the first and second contact elements 104, 106 at the receiving end of the scissor-like jaw 103, that is, the end of the scissor-like jaw 103 which is near arrow 120. The receiving ends 113, as depicted, of the first and second elements 104, 106 include angled sections 123 that are flanged outward such that an electrically conductive element (not shown in FIGS. 1B-1C) introduced into the jaw 103 in the direction of arrow 120, causes the angled sections 123 to deflect to receive the electrically conductive element (not shown in FIGS. 1B-1C). Thus, the electrically conductive element (not shown in FIGS. 1B-1C) will be guided between the contact elements 104, 106. This allows the scissor-like jaw 103 to accommodate an electrically conductive element without requiring a user to manually pull the first and second contact elements 104, 106 apart. The user may simply grasp the housing 102 in one hand and force a shaft into the scissor-like jaw 103 with the other.

According to one embodiment, both the first contact element 104 and second contact element 106 are formed of a conductive material. According to another embodiment only one of the first contact element 104 and the second contact element 106 is formed of a conductive material. Due to the conductive nature of one or both of the first and second contact elements 014, 106 an electrical connection can be created between the apparatus 100 and an electrically conductive element inserted into the scissor-like jaw 103. Because of this electrical connection, a voltage applied to one or both of the first and second contact elements 104, 106 will also be applied to the electrically conductive element.

Returning to FIG. 1A, the housing 102, according to one embodiment, has plurality of prongs 108-114 which extend from the body of the housing 102. The prongs 108-114 are not all visible in the depiction of FIG. 1A but are visible in other depictions. In FIG. 1A a first prong 108 and a second prong 110 are visible. A third prong 112, according to the side view of FIG. 1A is directly behind the first prong 108 and is not visible. A fourth prong 114, according to the side view of FIG. 1A is directly behind the second prong 110 and is not visible. A first gap 116 is formed with the first prong 108 and third prong 112 (not visible) above the gap 116 and the second prong 110 and fourth prong 114 (not visible) below the gap 116.

One of skill in the art will recognize that in certain embodiments the housing 102 may include more than four prongs 108-114. In other embodiments the housing may include fewer than four prongs 108-114. Further, one of skill in the art will recognize that the valleys 130 may include alternative shapes other than the substantially triangular shapes depicted in the illustrated embodiments. While only three valleys 130 are depicted in FIGS. 1A-1C, one of skill in the art will recognize that in certain embodiments the first contact element 104 and the second contact element 106 may include more than or less than three valleys 130.

The first gap 116 between the prongs 108, 110 acts as a guide for an electrically conductive element inserted into the scissor-like jaw 103. For example, the prongs 108, 110 restrict movement of an electrically conductive element in a vertical direction. This limits the amount of pressure that can be applied to the first and second contact elements 104, 106 reducing the likelihood of bending or damaging the first and second contact elements 104, 106. The first gap 116 also reduces the likelihood of contact between the hand of a user and the first and second contact elements 104, 106. This reduces the chance of electric shock for a user and reduces disruption of a current applied to the first and second contact elements 104, 106.

Figure 1D:
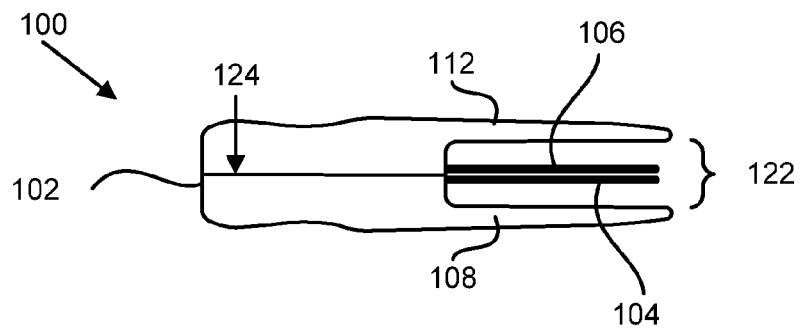
FIG. 1D is a top view of the apparatus of FIG. 1A, illustrating one embodiment of an apparatus for creating an electrical connection with an electrically conductive element.

Turning now to FIG. 1D a top view of the apparatus 100 from the direction of arrow 118 of FIG. 1A is shown. In this top view, the first prong 108 and the third prong 112 are visible. The second prong 110 is directly behind the first prong 108 and is not visible. The fourth prong 114 is directly behind the third prong 112 and is not visible. According to one embodiment, the housing 102 has a seam 124 along which separate pieces may be combined to form the housing 102. For example, separate plastic mold parts may be combined to form the housing 102.

The depiction of the apparatus 100 shown in FIG. 1D also illustrates an embodiment of the scissor-like nature of the scissor-like jaw 103. In one embodiment, the scissor-like jaw 103 is scissor-like because the first and second contact elements 104, 106 do not clamp directly opposite each other but rather slide past each other to a closed position. Thus, at least portions of each contact element 104 lie in separate parallel planes. According to the depicted embodiment, the first contact element 104 and the second contact element 106 extend from the housing 102 into a second gap 122 between the first prong 108 and the third prong 112. In certain embodiments the first contact element 104 lies substantially within a single plane that is substantially parallel to the second contact element 106. Thus, in one embodiment, rather than clamping directly opposite each other the first and second contact element 104, 106 scissor past each other from an open position to a closed position.

Also visible in the depiction of the electrical apparatus 100 of FIG. 1D is a second gap 122. The second gap 122 is formed with the first prong 108 and second prong 110 (not visible) below and the third prong 112 and fourth prong 114 (not visible) above. The second gap 122 allows the scissor-like jaw 103 to open wider than would otherwise possible if the prongs were solid and did not allow the first and second contact elements 104, 106 to move within the second gap 122 past the position of the prongs 108-114. The second gap 122 allows the first contact element 104 and the second contact element 106 to move past the prongs 108-114 when the first and second contact elements are moved in a direction perpendicular to the page, as depicted in FIG. 1D.

Figure 1E:
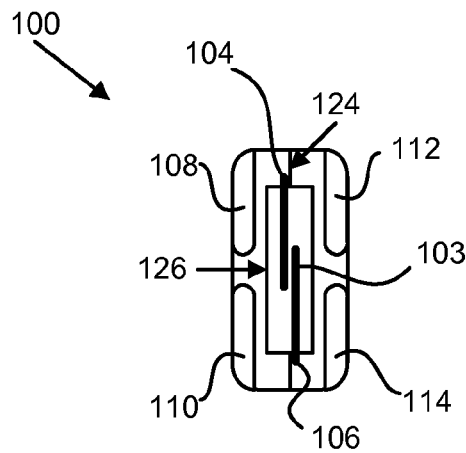
FIG. 1E is a cutaway end view of one embodiment of the apparatus of FIG. 1A depicting the first contact element and the second contact element in separate parallel planes.
Figure 1F:
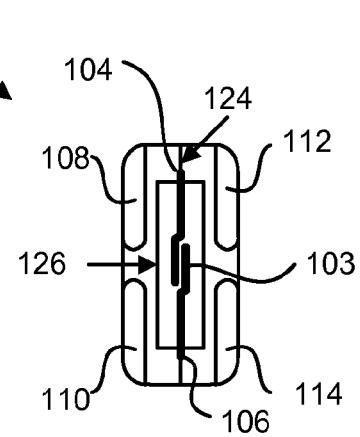
FIG. 1F is a cutaway end view according to another embodiment of the apparatus of FIG. 1A depicting a portion of the first contact element and the second contact element being positioned in the same plane.
Figure 1G:
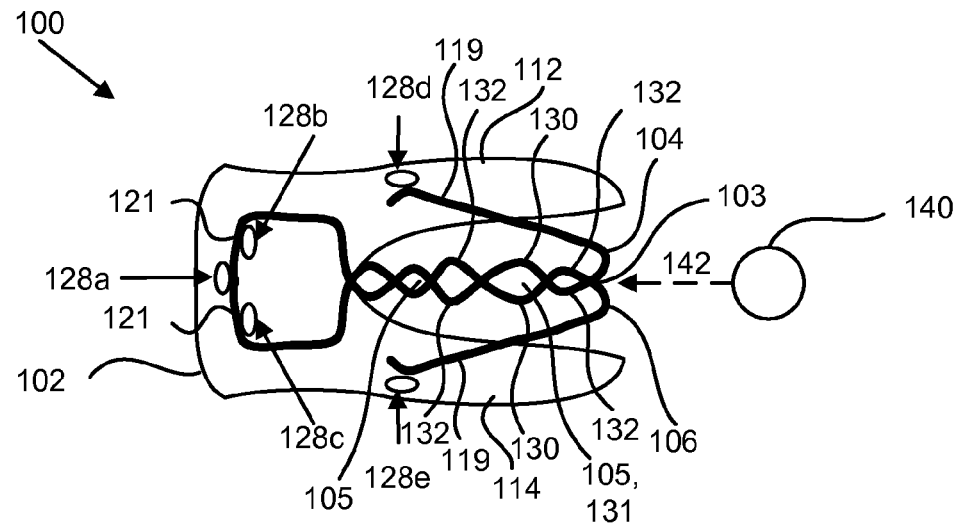
FIG. 1G is a cutaway side view of one embodiment of the apparatus of FIG. 1A prior to insertion of an electrically conductive element into the scissor-like jaw.
Figure 1H:
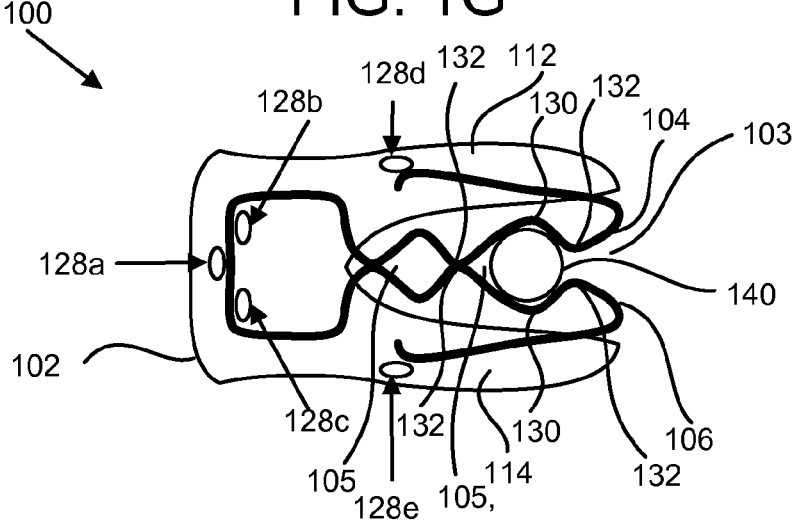
FIG. 1H is a cutaway side view of one embodiment of the apparatus of FIG. 1A engaging an electrically conductive element within the first stage of the scissor-like jaw.
Figure 1I:
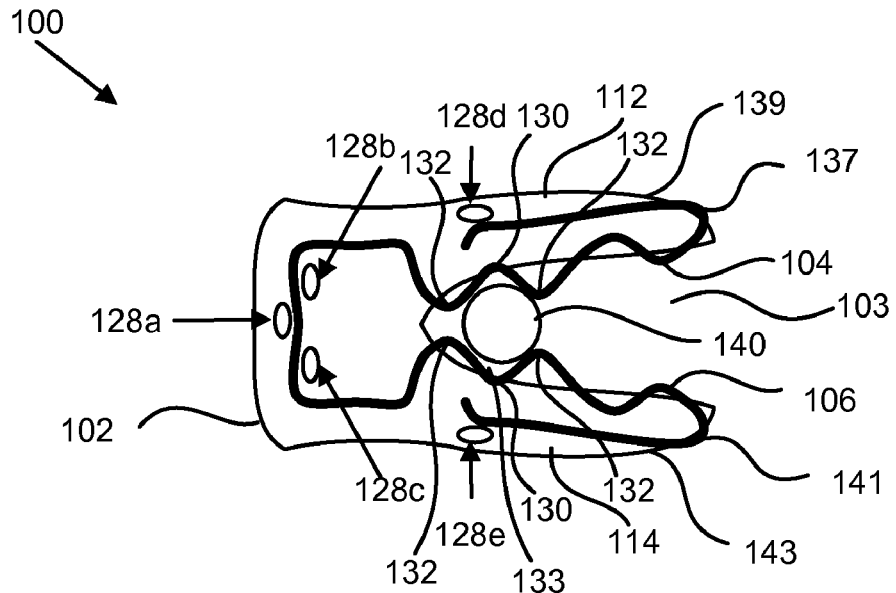
FIG. 1I is a cutaway side view of one embodiment of the apparatus of FIG. 1A engaging an electrically conductive element in the second stage of the scissor-like jaw.
Figure 1J:
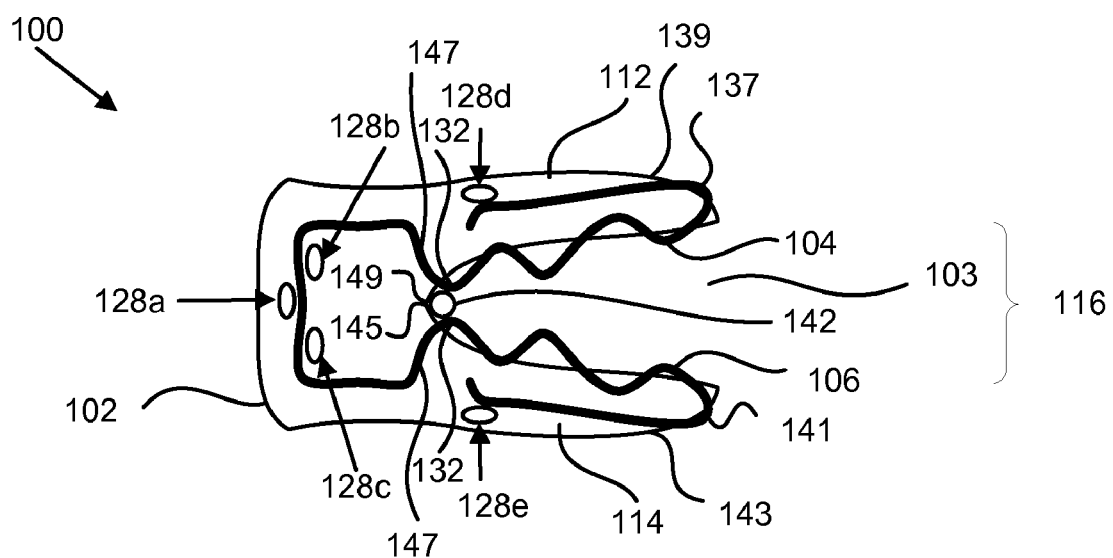
FIG. 1J is a cutaway side view of one embodiment of the apparatus of FIG. 1A engaging an electrically conductive element in the third stage of the scissor-like jaw.

As illustrated in FIGS. 1I and 1J discussed below, when a conductive shaft of electrically conductive element 140 is positioned within the scissor-like jaw 103, the contact elements 104, 106 may extend beyond the prongs 108-114 of the housing 102. Without the second gap 122 the prongs 108-114 may restrict the contact elements 104, and 106 from opening fully. In certain embodiments the housing 102 may be of a sufficient size to receive an electrically conductive element of a desired size range. Thus, one of skill in the art will recognize that in certain embodiments the second gap 122 may be omitted such that the prongs 108-114 restrict the contact elements 104, and 106 from opening at a position wider than the prongs 108-114. The gap 122, in certain embodiments, is at least wide enough to receive the first contact element 104 and the second contact element 106 when the first contact element 104 and the second contact element 106 are positioned adjacent to one another.

In certain embodiments the housing 102 may include two, rather than four, prongs 108-114. In such an embodiment, the prongs may extend from a common base and encompass at least a portion of the first and second contact elements 104, 106. In embodiments where the housing includes two prongs rather than four prongs, the two prongs may be engaged by the first and second contact element 104, 106 near the receiving end 113 of the scissor-like jaw 103 such that the two prongs provide support for biasing the first and second contact elements 104, 106 in the closed position.

In embodiments where the housing 102 includes two prongs without a second gap 122, a groove may be provided on the interior side of the two prongs, that is the side of the two prongs adjacent to the first and second contact elements 104, 106. The groove may allow the receiving end leveraging structures 119 of the first and second contact elements 104, 106 to slide within the groove to adjust a leveraging point along the two prongs.

Turning now to FIG. 1E depicting a cutaway end view of the apparatus 100 of FIG. 1A taken along line 1a and viewed from the direction of arrow 120. An opening 126 is depicted through which the first and second contact elements 104, 106 extend from within the housing 102. In the depicted embodiment, the first contact element 104 lies substantially in a single plane and the second contact element 106 lies substantially in a different, parallel plane. The scissor-like jaw 103 is shown in a closed position such that the first contact element 104 overlaps vertically with the second contact element 106. That is, the bottom of the first contact element 104 extends below the top of the second contact element 106. The end view of FIG. 1E is exemplary according to one embodiment of the scissor-like jaw 103.

FIG. 1F depicts an alternate cutaway end view of the apparatus 100 of FIG. 1A taken along line 1a and viewed from the direction of arrow 120, according to another exemplary scissor-like jaw 103. An opening 126 is depicted through which the first and second contact elements 104, 106 extend from within the housing 102. In this depicted embodiment a portion of both the first contact element 104 and the second contact element 106 lie substantially in the same plane while a portion of each lie within different substantially parallel planes. More specifically, the portion of the first and second contact elements 104, 106 that overlap vertically lie in separate, substantially parallel planes.

FIGS. 1E and 1F also depict the first prong 108, second prong 110, third prong 112, and fourth prong 114 which extend from the housing 102 and are substantially parallel to the first and second contact elements 104, 106. Additionally, a seam 124 of the housing 102 along which separate pieces are combined to form the housing 102 is also shown.

FIG. 1G is a cutaway side view of the apparatus 100, with the cutaway taken along the seam 124 of FIGS. 1D-1F. The cutaway view illustrates a one embodiment of a manner in which portions of the first and second contact elements 104, 106 engage the housing 102. According to the depicted embodiment, the first and second contact elements 104, 106 are formed of a single component. The single component may be formed using wireform techniques or other techniques, such as molding, known within the art. Other embodiments may include first and second contact elements 104, 106 formed of separate components, such as wireform components. Wireform components are formed by bending an elongate piece of metal, like a wire, and shaping it into a desired form. Still other embodiments may include a similar component that has been formed in a variety of manners, including methods of shaping metal or other conductive materials that are well known in the art.

According to the depicted embodiment, the housing 102 includes a number of structural elements 128a-128e to engage the receiving end leveraging structures 119 of the first and second contact elements 104, 106, the recessed end leveraging structures 121 of the first and second contact elements 104, 106, or both.

In the embodiment illustrated in FIG. 1G, the housing 102 includes retaining structural elements 128a-128c which maintain at least a portion of the recessed end leveraging structures 121 of the first and second contact elements 104, 106 in substantially the same position within the housing 102. As will be understood by one skilled in the art in light of the present disclosure, the retaining structural elements 128a-128c depicted are only exemplary. The retaining structural elements 128a-128c may number fewer or greater than the three shown and may vary greatly in orientation, size, and shape.

In the depicted embodiment, the housing also comprises leveraging structural elements 128d-128e positioned on prongs 112 and 114. The leveraging structural elements 128d and 128e are leveraged by the receiving end leveraging structures 119 of the first contact element 104 and the second contact element 106, respectively, to bias the scissor-like jaw 103 towards a closed position. For example, the wireform component, of which the first contact element 104 and second contact element 106 are formed, may be resiliently deformed to receive a shaft of an electrically conductive element 140 as illustrated in FIG. 1H. In FIG. 1G, the scissor-like jaw 103 formed by the first and second contact elements 104, 106 is shown in a closed position. Again as will be understood by one skilled in the art in light of the present disclosure, the leveraging structural elements 128d-128e depicted are only exemplary. The leveraging structural elements 128d-128e may number fewer or greater than the two shown and may vary greatly in orientation, size, and shape. For example, in one embodiment, portions of walls of the prongs 108-114 of the housing 102 may act as leveraging structural elements.

In certain embodiments the structural elements 128a-e may include channels within the housing 102 that engage the first and second element 104, 106 to bias the first and second elements 104, 106 in the closed position. In another embodiment, the housing 102 may be molded around portions of the first and second contact elements 104, 106 such that the housing 102 supports the first and second contact elements 104, 106 in a closed position.

Also shown in FIG. 1G is a shaft of an electrically conductive element 140, before it has been inserted into the scissor-like jaw 103. The shaft of the electrically conductive element 140 is depicted with its axis transverse to the page such that only the cross section of the shaft 1 of the electrically conductive element 40 is shown. The cross section of the shaft of the electrically conductive element 140 is depicted as being circular but other cross-sectional shapes are also possible. In certain embodiments the electrically conductive element 140 may be a substantially planar sheet and thus may not include a shaft. In the embodiment illustrated in FIG. 1G the electrically conductive element 140 may be inserted into the scissor-like jaw 103 by forcing it between the first and second contact elements 104, 106 in the direction of arrow 142. For example, a user may manually grasp the housing 102 in one hand and force the shaft of the electrically conductive element 140 into the scissor-like jaw 103 with the other hand.

As the electrically conductive element 140 is forced against the first and second contact elements 104, 106, the first contact element 104 is displaced upward and the second contact element 106 is displaced downward, according to the orientation of the side view of FIG. 1G. In certain embodiments only one of the first contact element 104 or the second contact element 106 is moveable while the other contact element is rigidly fixed. In such an embodiment the movable contact element may be displaced upward or downward to receive the electrically conductive element 140.

Because the first and second contact elements 104, 106 are biased against the leveraging structural elements 128d, 128e, the scissor-like jaw 103 widens and narrows depending on the position of the shaft of the electrically conductive element 140 in the scissor-like jaw 103. That is, because of the resilient nature of the first and second contact elements 104, 106 the scissor-like jaw 103 closes around the electrically conductive element 140 placed within the scissor-like jaw 103 as far as permitted by the electrically conductive element 140 depending on the electrically conductive element's 140 position within the scissor-like jaw 103. For example, as the shaft of the electrically conductive element 140 moves towards a peak 132 within the scissor-like jaw 103, the scissor-like jaw widens as the first contact element 104 is pushed upward and the second contact element 106 is pushed downward. As the shaft of the electrically conductive element 140 moves from a peak 132 towards a valley 130 the first contact element 104 resiliently moves downward and the second contact element 106 resiliently moves upward. Thus, the contact elements 104, 106 remain in contact with the shaft of the electrically conductive element 140 as long as the electrically conductive element 140 is positioned within the scissor-like jaw 103. When the electrically conductive element 140 is removed, the scissor-like jaw 103 automatically returns to its closed position by operation of the resilient nature of the first and second contact element 104, 106, as depicted in FIG. 1G.

FIG. 1H depicts one embodiment of the apparatus 100 with the shaft of the electrically conductive element 140 inserted into the scissor-like jaw 103 in the direction of the arrow 142 of FIG. 1G. The shaft 140 is shown resting in a first stage 131 of the scissor-like jaw 103. The first stage 131 is formed between a valley 130 of the first contact element 104 and a valley 130 of the second contact element 106. Peaks 132 on either side of the valleys 130, in conjunction with the biasing of the first and second contact elements 104, 106 towards a closed position, help to maintain the electrically conductive element 140 within the first stage 131. The valleys 130 and peaks 132 allow the shaft 140 to be maintained in the stage 131 even with very little tension. The small amount of tension allows the shaft of the electrically conductive element 140 to be rotated in relation to the contact elements 104, 106 without losing the electrical connection between the contact elements 104, 106 or allowing the shaft of the electrically conductive element 140 to slip out of the scissor-like jaw 103. Thus, a user can use the apparatus 100 to apply a voltage to a conductive shaft of the electrically conductive element 140 while still allowing the user to use the shaft of the electrically conductive element 140 for other purposes. For example, a surgeon could use the apparatus 100 to apply a voltage to the shaft of a surgical tool and still be able to use the surgical tool for its normal purpose, which may involve rotation of the shaft. In another example, a mechanic or other skilled tradesman may apply a voltage to a shaft of a tool while still being able to manipulate the tool.

The scissor-like nature of the scissor-like jaw 103 allows the apparatus 100 to engage shafts having signification variation in cross-sectional size. Because the first contact element 104 and the second contact element 106 scissor past each other towards a closed position, the scissor-like jaw 103 can engage a shaft of any diameter between being completely closed and width of the first gap 116. In other words, the scissor-like nature allows the scissor-like jaw 103 to engage shafts having diameters much smaller or much larger than the depth of the valleys 130. For example, the first stage 131, in which the shaft 140 is depicted, could also engage a shaft having a smaller diameter or a larger diameter because as the first contact element 104 and the second contact element 106 slide past each other the size of the stage 131 is increased or decreased due to the tapered nature of the valleys 130.

FIG. 1I depicts the shaft of the electrically conductive element 140 after it has been forced deeper into the scissor-like jaw 103 such that it now rests in a second stage 133 of the scissor-like jaw 103. The second stage 133 is formed between a valley 130 of the first contact element 104 and a valley 130 of the second contact element 106. Similar to the first stage 131, peaks 132 on either side of the valleys 130, in conjunction with the biasing of the first and second contact elements 104, 106 towards a closed position help to maintain the shaft of the electrically conductive element 140 within the second stage 133. The placement of the shaft of the electrically conductive element 140 alternately within the first stage 131, as in FIG. 1H, or in the second stage 133, as in FIG. 1I, illustrate that a shaft of the electrically conductive element 140 may be selectively engaged in different stages 105.

The placement of the shaft of the electrically conductive element 140 within the first stage 131 (FIG. 1H) and the second stage 133 (FIG. 1I) provides different amount of tension between the shaft of the electrically conductive element 140 and the first and second elements 104, 106. This is because the first and second contact elements 104 106 are typically be more extremely deformed for placement of the shaft of the electrically conductive element 140 in the second stage 133 rather than the first stage 131. This gives a user the option of adjusting the amount of tension provided between the contact elements 104, 106 and the shaft of the electrically conductive element 140. For example, it may be desirable to have greater tension to hold the shaft of the electrically conductive element 140 more firmly or create a better electrical connection. On the other hand, it may be desirable to have less tension to allow the shaft of the electrically conductive element 140 to rotate more freely in relation to the first and second elements 104, 106. By moving the shaft 140 to a deeper position within the scissor-like jaw 103 the tension of the second elements 104, 106 on the shaft of the electrically conductive element 130 is increased. For a lighter application, the shaft of the electrically conductive element 140 may be placed at a shallower position within the scissor-like jaw 103.

The multiple number of stages 105 also allows for a greater variety in the cross sectional sizes of shafts that can be engaged within the apparatus 100. The peaks 132 and valleys 130 may vary in size to accommodate different shafts that fall within a different size range. For example, the peaks 132 and valleys 130 of the first stage 131 may be larger than the peaks 132 and valleys 130 of the second stage 133. Additionally, the peaks 132 and valleys 130 of a third stage (not shown) may also vary. In an alternate or additional embedment, a stage 105 may also be limited in size of shafts it may accommodate by the housing 102. For example, the width of the first gap 116 may only fit shafts having cross sectional sizes less than the width of the gap 116 at the corresponding stage.

With reference again to FIG. 1I the upper portion 137 of the first contact element 104 is extending above the upper portion 139 of the first prong (not shown) and the third prong 112. The lower portion 141 of the second contact element 106 is extending below the lower portion 143 of the second prong 110 (not shown) and the fourth prong 114. This is possible because of the second gap 122 shown in FIG. 1D. Because of the second gap 122, the prongs 108-114 do not limit how wide the scissor-like jaw 103 may open. This enables the first and second contact elements 104, 106 to be displaced to a greater extent to accommodate larger ranges of cross-sectional shaft sizes.

Turing now to FIG. 1J a shaft of a electrically conductive element 142 having a much smaller cross-sectional size than that of the shaft of the electrically conductive element 140 of FIGS. 1G-1I is shown. The shaft 142 is shown within a third stage 145 of the scissor-like jaw 103. However, it may also be able to engage the shaft 142 within one or both of the first stage 131 or second stage 133. The third stage 145 is partially formed between a retreating portion 147 of the first contact element 104 and a retreating portion 147 of the second contact element. The housing 102 prevents the shaft 142 from sliding into the bottom of the retreating portions 147 of the first and second contact elements 104, 106. Thus, the width of the first gap 116 at the position, 149 of the third stage is limiting the size of a shaft that can be accommodated in the third stage 145. The shaft of the electrically conductive element 142 is engaged not only by the first contact element 104 and second contact element 106, but also by the housing 102. Thus, not only do peaks 132 of the first and second contact elements 104, 106 help retain the shaft of the electrically conductive element 142 within the third stage 145, but the housing 102 also limits movement of the shaft of the electrically conductive element 142.

As will be understood by one skilled in the art in light of the present disclosure, the apparatus 100 of FIGS. 1A-1J is only exemplary and significant variation is possible without departing from the teaching and scope of the present disclosure. For example, the scissor-like jaw 103 illustrated and described in relation to FIGS. 1A-1J is only exemplary. Scissor-like jaws of other configurations, shapes and configurations are also possible. For example, the first and second contact elements 104, 106 may be more rigid than the flexible and resilient structure shown in FIGS. 1A-1J. Additionally, the peaks 132 and valleys 130 may vary in shape, size, number, or geometry. Jaws that are not scissor-like may also be employed. For example, clamping jaws, wherein the first and second contact element 104, 106 directly oppose each other and do not scissor past each other are possible. Additional variation is possible in that only one of the first and second contact elements 104, 106 may have peaks 132 and valleys 130.

With the apparatus 100 of FIGS. 1A-1J a voltage can be applied to a variety of surgical tools so that the tool can be used for its ordinary function as well as locating a nerve. This allows a single surgeon or medical staff to simultaneously perform medical procedures and apply electrical stimulation with the use of a standard surgical tool. Additionally, because the apparatus 100 allows a shaft of an electrically conductive element 140 engaged in one of the stages 105 to rotate, surgical tools that need to be rotated or manipulated during use will not be hampered by the connection to the apparatus 100. While the embodiments discussed herein are directed to an electrical clip for a surgical device, one of skill in the art will recognize that the apparatus 100 may be useful in any environment in which an electrical current is to be delivered to a conductive element. Such applications may include, but are not limited to, automotive applications, computer science applications, electrical and structural wiring applications, etc.

In certain embodiments the apparatus 100 may include an electrical connector coupled to at least one of the first contact element 104 or the second contact element 106 to apply a voltage to the electrically conductive element 140. A voltage may be applied to one or more of the contact elements 104, 106 in a variety of manners. For example varying types of connectors, wires, and cables could be attached to one or both of the contact elements 104, 106 to connect them to an electrical source. Connecting an electrical source to the apparatus 100 will be discussed in further detail in relation to FIG. 4A.

Turning now to FIGS. 2A-2E another embodiment of apparatus 200 for creating an electrical connection with an electrically conductive element is shown. The apparatus 200 is substantially similar to the apparatus 100 of FIGS. 1A-1J. Differences between the apparatus 200 of FIGS. 2A-2E and the apparatus 100 of FIGS. 1A-1J include a single stage 205 in a scissor-like jaw 203 and a housing 202 that does not include any prongs.

Figure 2A:
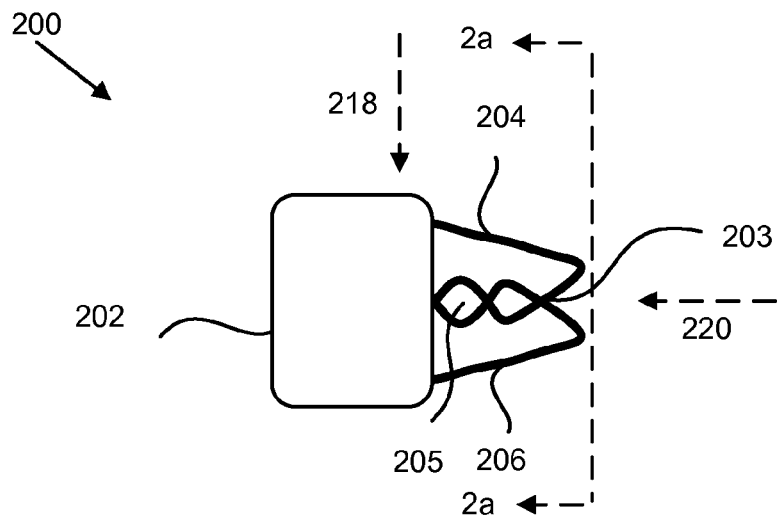
FIG. 2A is a side view illustrating one embodiment an apparatus for creating an electrical connection with an electrically conductive element.

FIG. 2A is a side view of an apparatus 200 for creating an electrical connection with an electrically conductive element (not shown in FIG. 2A). The apparatus 200 includes a housing 202, a first contact element 204, and a second contact element 206. In this embodiment, the housing does not include prongs. Instead the first and second contact elements 202, 204 are connected to the housing to provide a resilient force to bias the contact elements 202, 204 into a closed position. The first contact element 204 and the second contact element 206 are opposing contact elements that form a scissor-like jaw 203 to engage an electrically conductive element (not shown in FIG. 2A), similar to the first and second contact elements 104, 106 of FIGS. 1A-1J. For example, an electrically conductive element (not shown in FIG. 2A) may be inserted into the scissor-like jaw 203 with the first contact element 204 above and the second contact element 206 below. When the scissor-like jaw 203 is in a closed position, as depicted, the first contact element 204 overlaps vertically with the second contact element 206.

Figure 2B:
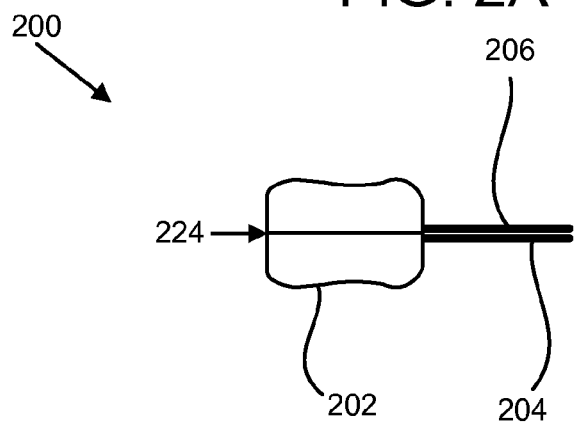
FIG. 2B is a top view illustrating one embodiment of the apparatus of FIG. 2A.

FIG. 2B is a top view of the apparatus 200 viewed along line 2a in the direction of arrow 218 of FIG. 2A. From this view, the housing 202 and a seam 224, along which separate pieces are combined to form the housing 102, are shown. Additionally, the first contact element 204 and the second contact element 206 are shown. Similar to the view of FIG. 1D, the first and second contact elements 204, 206 lie in separate, substantially parallel planes. In certain embodiments the housing 202 may be a single piece molded around the first contact element 204 and the second contact element 206. One of skill in the art will recognize that where the housing 202 includes separate pieces, the seam 224 may be located elsewhere.

Figure 2C:
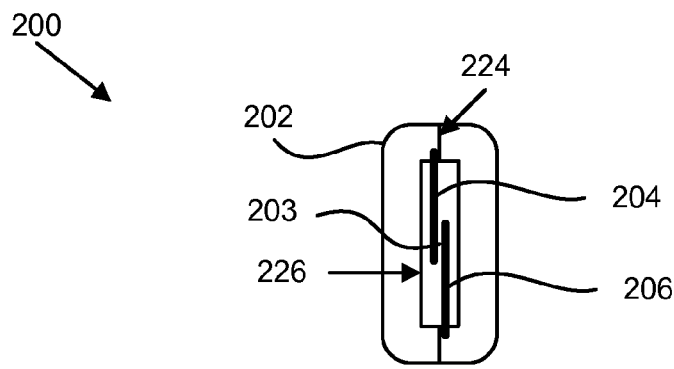
FIG. 2C is an end view of the apparatus of FIG. 2A depicting the first contact element and the second contact element in separate parallel planes.

FIG. 2C is an end view of the apparatus 200 in the direction of arrow 220 of FIG. 2A. An opening 226 is depicted through which the first and second contact elements 204, 206 extend from within the housing 202. In the depicted embodiment, the first contact element 204 lies substantially in a first plane and the second contact element 206 lies in a different, substantially parallel plane. The scissor-like jaw 203 is shown in closed position such that the first contact element 204 overlaps vertically with the second contact element 206. That is, the bottom of the first contact element 204 extends below the top of the second contact element 206.

Figure 2D:
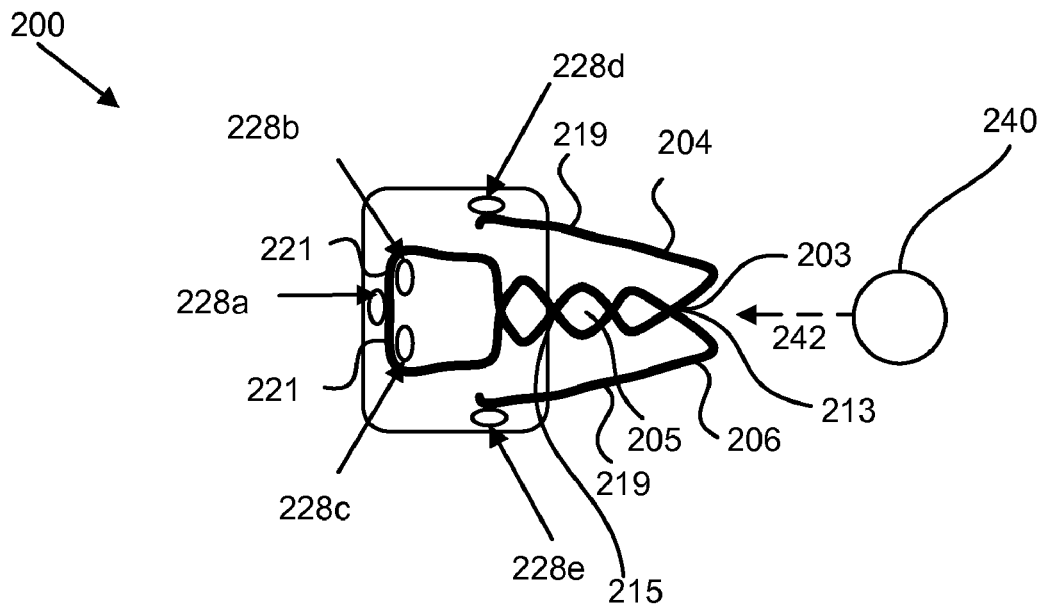

FIG. 2D is a cutaway side view of the apparatus 200, cutaway along the seam 224 of FIGS. 2B-2C. The cutaway view illustrates an exemplary manner in which portions of the first and second contact elements 204, 206 extend into and engage the housing 202 to bias the scissor-like jaw 203 in the closed position. According to the depicted embodiment, the first and second contact elements 204, 206 are formed of a single wireform component. Other embodiments may include first and second contact elements 204, 206 formed of separate wireform components. The wireform of the first and second contact elements 204, 206 has a structural resiliency sufficient to resiliently bias the scissor-like jaw 203 in the closed position.

The housing 202 of the apparatus 200 includes a number of structural elements 228a-228e that engage the first and second contact elements 204, 206. Specifically, retaining structural elements 228a-228c maintain at least portions of the first and second contact elements 204, 206 in substantially the same position within the housing 202. The housing also includes leveraging structural elements 228d-228e. The leveraging structural elements 228d and 228e are leveraged by the first contact element 204 and the second contact element 206, respectively, to bias the scissor-like jaw 203 towards a closed position.

As with the embodiments described above, in certain embodiments the structural elements 228a-228e may include channels within the housing 202 that receive portions of the first and second contact elements 204,206 to bias the scissor-like jaw 203 in the closed position. In other embodiments, the housing may be molded around a portion of the first and second contact element to hold the first and second contact element 204, 206 in a position that biases the scissor-like jaw 203 in a closed position.

In certain embodiments the first contact element 204 and the second contact element 206 include a receiving end leveraging structure 219 and a recessed end leveraging structure 221. The receiving end leveraging structures 219 may engage the retaining structural elements 228d-228e to bias the scissor-like jaw 203 in the closed position. Similarly, the recessed end leveraging structures 221 may engage the retaining structural elements 228a-228c to bias the scissor-like jaw 203 in the closed position. In one embodiment the receiving end leveraging structures 219 rigidly engage the housing to bias the scissor-like jaw 203 in the closed position while the recessed end 215 of the scissor-like jaw 203 remains unengaged and free floating. In another embodiment the recessed end leveraging structures 221 rigidly engage the housing to bias the scissor-like jaw 203 in the closed position while the receiving end 213 of the scissor-like jaw 203 remains unengaged and free floating. In the embodiment illustrated in FIG. 2D both the receiving end leveraging structure 219 and the recessed end leveraging structure 221 are engaged with the housing 202 to bias scissor-like jaw 203 in the closed position.

A shaft of an electrically conductive element 240, before insertion into the scissor-like jaw 203, is also shown. The electrically conductive element 240 is depicted with its axis transverse to the page such that only the cross section of the shaft electrically conductive element 240 is shown. The cross section of the shaft electrically conductive element 240 is depicted as being circular but other cross-sectional shapes are also possible. In certain embodiments the electrically conductive element 240 may not include a shaft at all. For example, in one embodiment the electrically conductive element 240 may be substantially planar. In another embodiment the electrically conductive element 240 may include a substantially planar element having raised portions that are received within the stage 205. In such an embodiment the stage 205 may restrict the withdrawal of the electrically conductive element 240 from within the scissor-like jaw 203 by engaging the raised portions on the electrically conductive element 240.

In the embodiment illustrated in FIG. 2D the electrically conductive element 240 includes a shaft. The shaft of the electrically conductive element 240 may be inserted into the scissor-like jaw 203 by forcing it between the first and second contact elements 204, 206 in the direction of arrow 242. As the shaft of the electrically conductive element 240 is forced against the first and second contact elements 204, 206 in the direction of the arrow 242, the first contact element 204 is displaced upward and the second contact element 206 is displaced downward, according to the depicted orientation. Because the first and second contact elements 204, 206 are biased against the leveraging structural elements 228d, 228e, the scissor-like jaw 203 widens and narrows depending on the position of the shaft of the electrically conductive element 240 in the scissor-like jaw 203. In other words, the first and second contact elements 204, 206 remain in contact with the shaft of the electrically conductive element 240 when is the shaft is positioned within the scissor-like jaw 203.

In one embodiment the amount of biasing force applied to the first contact element 204 is different than the biasing force applied to the second contact element 206. For example, in certain embodiments the wireform of the first contact element 204 may be larger or smaller or may be made of a material having a higher or lesser structural resiliency than the size or the material of the second contact element 204.

Figure 2E:
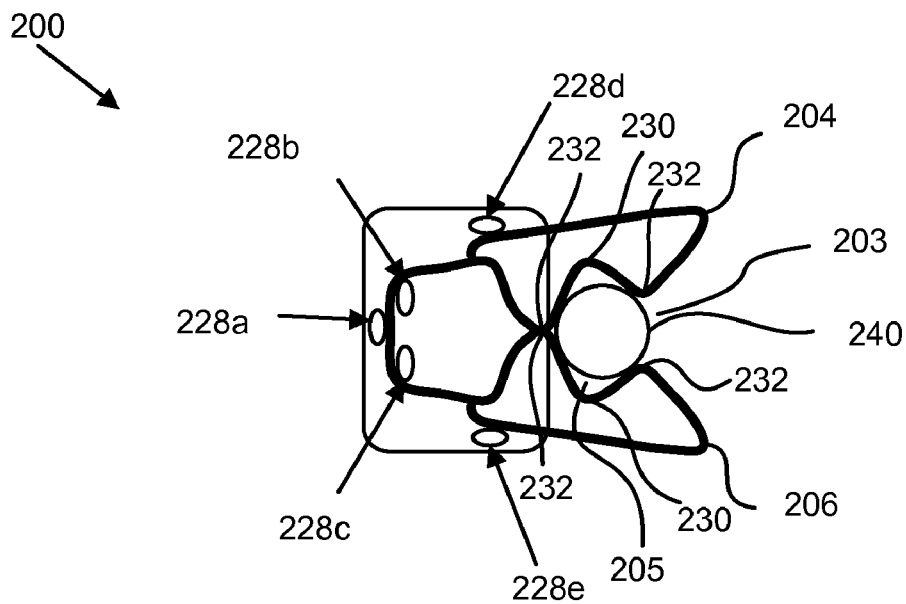
FIG. 2E is a cutaway side view of one embodiment of the apparatus of FIG. 2A engaging an electrically conductive element within a single stage in the scissor-like jaw.

FIG. 2E depicts the shaft of the electrically conductive element 240 after it has been inserted into the scissor-like jaw 203 of the apparatus 200 along the arrow 242 of FIG. 2D. The shaft 240 is shown resting in a stage 205 of the scissor-like jaw 203. The stage 205 is formed between a valley 230 of the first contact element 204 and a valley 230 of the second contact element 206. Peaks 232 on either side of the valleys 230, in conjunction with the biasing of the first and second contact elements 204, 206 towards a closed position, help to maintain the shaft 240 within the stage.

Turning now to FIGS. 3A-3E a further exemplary embodiment of an apparatus 300 for creating an electrical connection with an electrically conductive element is shown. The apparatus 300 includes a housing 302 with prongs 308, 310, 312, 314 substantially similar to the housing 102 and prongs 108-114 of the apparatus 100 of FIGS. 1A-1J. The apparatus 300 also includes a first contact element 304 for engaging a first side of an electrically conductive element and a second contact element 306 for engaging a second side of an electrically conductive element. In the depicted embodiments the first and second contact elements 304, 306 may be more rigid structures than the first and second contact elements 104, 106 of FIGS. 1A-1J. Additionally, in certain embodiments, the contact elements 304, 306 may be positioned in a single common plane such that the first and second contact elements 304, 306 clamp against each other to form a clamp-like jaw 303 rather than a scissor-like jaw. In other embodiments the contact elements 304 and 306 may be oriented on separate planes and may operate as a scissor-like jaw substantially similar to the scissor-like jaw 103 of FIGS. 1A-1J.

Figure 3A:
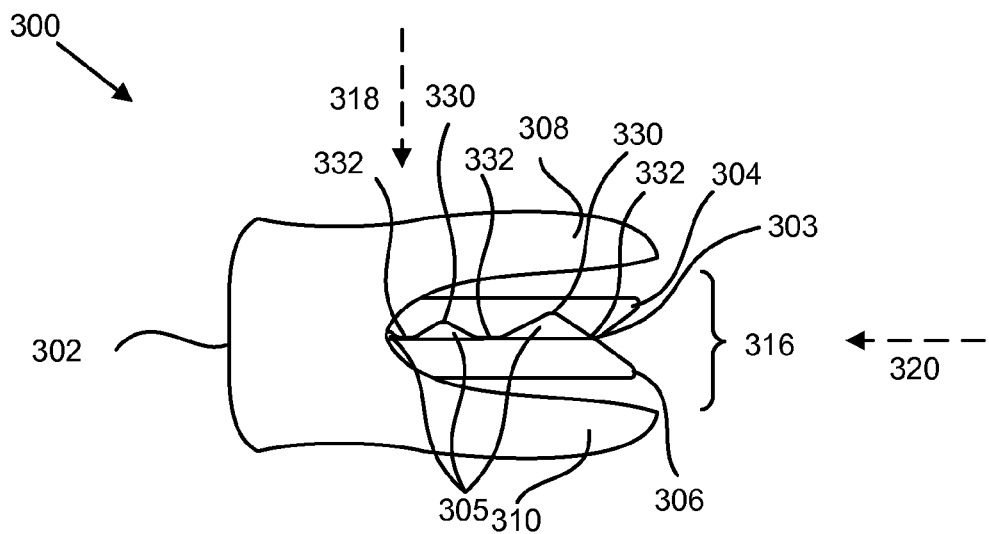
FIG. 3A is a side view illustrating one embodiment an apparatus for creating an electrical connection with an electrically conductive element.

FIG. 3A depicts a side view of an apparatus 300 for creating an electrical connection to an electrically conductive element. The apparatus 300 includes a housing 302, a first contact element 304 and a second contact element 306. The housing 302 is illustrated as being similar to the housing 102 of FIGS. 1A-1J. The first contact element 304 and second contact element 306 are opposing contact elements that form a clamp-like jaw 303 to engage a conductive shaft, wherein the contact elements 304, 306 do not slide past each other to a closed position but rather clamp directly against and opposite each other. Additionally, in the depicted embodiment, only the first contact element 304 includes valleys 330 and peaks 332 that create stages 305. The second contact element 306 is straight without peaks or valleys. According to other embodiments, one of or both of the first and second contact elements 304, 306 include valleys 330 and peaks 332. One of skill in the art will recognize that in certain embodiments the first and second contact elements 304, 306 may be made of wireform substantially similar to the wireform contact elements 104, 106, and 204, 206 illustrated in the embodiments of FIGS. 1A-2E. In the depicted embodiment, the first contact element 304 and the second contact element 306 are substantially planar contact elements. In certain embodiments only one of the first and second contact elements 304, 306 are made of an electrically conductive material. In another embodiment, only one of the first and second contact elements 304, 306 is moveable while the other contact element remains in substantially the same position relative to the housing 302.

Similar to apparatus 100, and apparatus 200, an electrically conductive element may be inserted into the jaw with the first contact element 304 above and the second contact element 306 below. When the clamp-like jaw 303 is in a closed position, as depicted, the first contact element 304 clamps against and directly opposite the second contact element 306.

The housing 302, according to the depicted embodiment, includes plurality of prongs 308-314 which extend from the body of the housing 302. The prongs are not all visible in the depiction of FIG. 3A but are visible in other depictions. In FIG. 3A a first prong 308 and a second prong 310 are visible. A third prong 312, according to the side view of FIG. 3A, is directly behind the first prong 308 and is not visible. A fourth prong 314, according to the side view of FIG. 3A, is directly behind the second prong 310 and is not visible. A first gap 316 is formed with the first prong 308 and third prong 312 (not visible) above the first gap 316 and the second prong 310 and fourth prong 314 (not visible) below the first gap 316.

A number of stages 305 are formed between the first contact element 304 and the second contact element 306. According to the depicted embodiment, three valleys 330 are formed in the first contact element 304 such that electrically conductive elements of varying size ranges may be engaged in each stage 305. A first stage 305 is formed between the biggest valley 330 in the first contact element 304 and the second contact element 306. A second stage 305 is formed between the neighboring valley 330 in the first contact element 304 and the second contact element 306. A third stage 305 is formed between an additional valley 330 (only partially visible) of the first contact element 304, the second contact element 306, and the housing 302. While only three stages 305 are illustrated, one of skill in the art will recognize that in certain embodiments the clamp-like jaw 303 may include additional valleys creating additional stages.

Figure 3B:
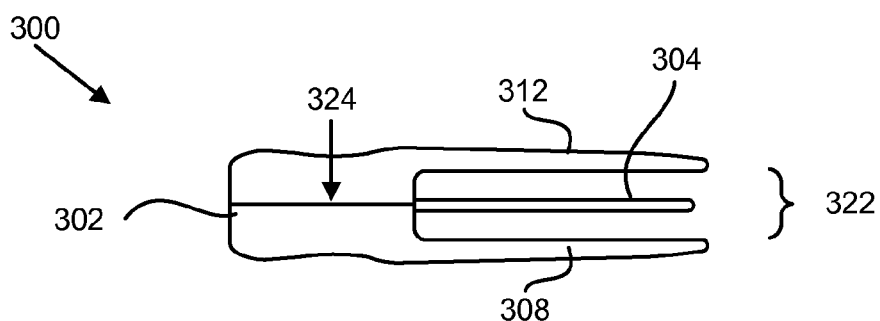
FIG. 3B is a top view illustrating one embodiment of the apparatus of FIG. 3A.

FIG. 3B depicts a view of the apparatus 300 from the direction of arrow 318 of FIG. 3A. In this view, the first prong 308 and the third prong 312 are visible. The second prong 310 is directly behind the first prong 308 and is not visible. The fourth prong 314 is directly behind the third prong 312 and is not visible. A vertical gap 322 is formed, according to the top view of FIG. 3D, with the first prong 308 and second prong 310 (not visible) below and the third prong 312 and fourth prong 314 (not visible) above. According to one embodiment, the housing 302 includes a seam 324 along which separate pieces of the housing 302 are combined to form the housing 302.

Also shown in the view of FIG. 3B is the first contact element 304. The first contact element 304 lies substantially within the same plane as the second contact element 306 and thus blocks view of the second contact element 306 in FIG. 3B.

Figure 3C:
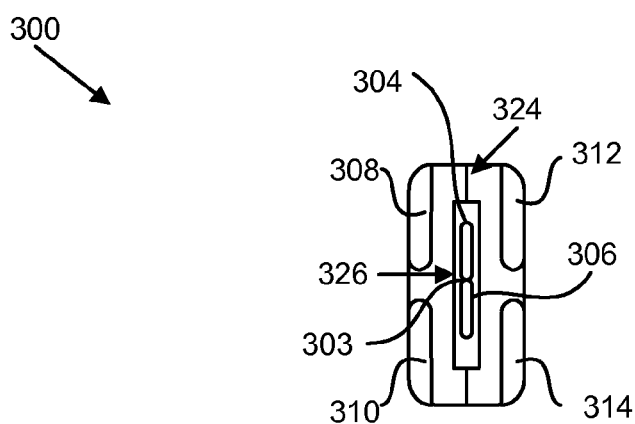
FIG. 3C is an end view of the apparatus of FIG. 3A depicting the first contact element and the second contact element in the same plane such that the first and second contact element form a clamp-like jaw.

FIG. 3C depicts an end view of the apparatus 300 of FIG. 3A in the direction of arrow 320, according to one exemplary embodiment. An opening 326 is depicted through which the first and second contact elements 304, 306 extend from within the housing 302. In the depicted embodiment, the first contact element 304 lies substantially within the same plane as the second contact element 306. The clamp-like jaw 303 is shown in a closed position such that the first contact element 304 clamps against the second contact element 306. That is, the bottom of the first contact element 304 extends up against the top of the second contact element 306. Thus, instead of sliding past each other to a closed position similar to a scissor, the contact elements 304 and 306 push against each other, similar to a clamp.

FIG. 3C also depicts the first prong 308, second prong 310, third prong 312, and fourth prong 314 which extend from the housing 302 and are substantially parallel to the first and second contact elements 304, 306. Additionally, the seam 324 of the housing 302 along which separate pieces are combined to form the housing 302 is also shown in FIG. 3C.

Figure 3D:
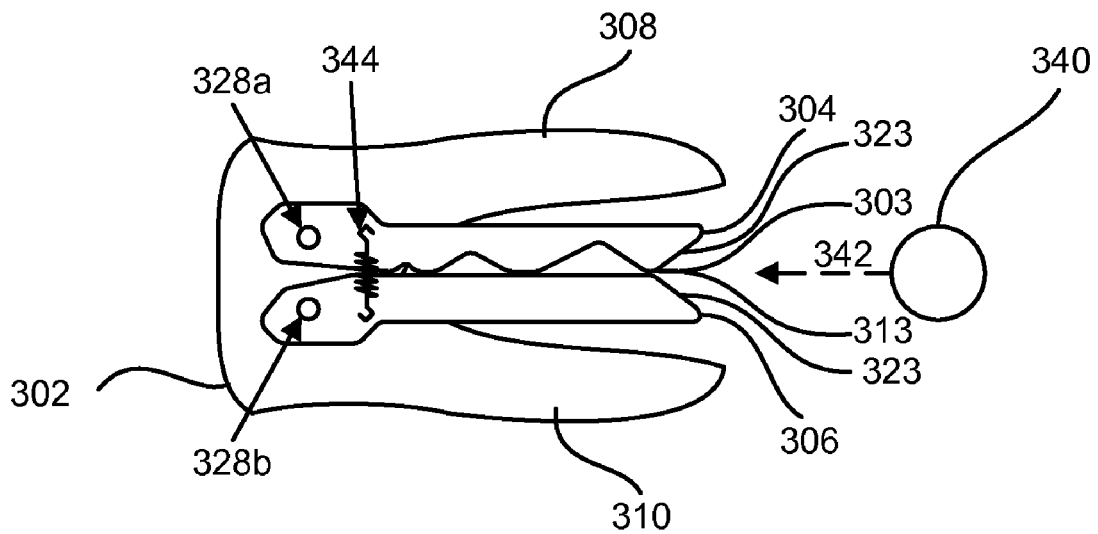
FIG. 3D is a cutaway side view of one embodiment of the apparatus of FIG. 3A prior to insertion of an electrically conductive element into the scissor-like jaw.

Turning now to FIG. 3D, a cutaway side view of the apparatus 300, cutaway along the seam 324 of FIGS. 3B-3C is shown. The cutaway view illustrates an exemplary embodiment in which portions of the first and second contact elements 304, 306 extend into and engage the housing 302 in a clamp-like configuration. Other embodiments may include first and second contact elements 304, 306 formed of a single component.

The housing 302 includes a number of structural elements 328a-328b to engage the first and second contact elements 304, 306. Specifically, the housing 302 includes retaining structural elements 328a-328b which extend through holes in the first and second contact elements 304, 306, respectively. The retaining structural elements 328a, 328b act as pivots for the first and second contact elements 304, 306 allowing them to rotate relative to the housing 302. A biasing element 344 is coupled to the first contact element 304 and the second contact element 306 to bias the first contact element 304 and the second contact element 306 towards each other such that the clamp-like jaw 303 is resiliently biased towards a closed position. In certain embodiments the biasing element 344 may be coupled to only one of the first contact element 304 or the second contact element 306 with the other contact element 304, 306 remaining in a fixed position. In such an embodiment the biasing element 344 operates to bias either the first contact element 304 or the second contact element towards the fixed contact element 304, 306 and position the clap-like jaw 303 in the closed position. In the embodiment illustrated in FIG. 3D the biasing element 344 is a spring. In other embodiments the biasing element 344 may be made of an elastic material coupled to the first contact element 304, the second contact element 306, or both to bias the clamp-like jaw 303 in the closed position. As will be clear to one skilled in the art in light of the present disclosure, numerous other structures and methods may be used to retain and/or bias the first and second contact elements 304, 306 within the housing 302.

A shaft of an electrically conductive element 340, before insertion into the clamp-like jaw 303, is also shown in FIG. 3D. The shaft of the electrically conductive element 340 is depicted with its axis transverse to the page such that only the cross section of the shaft of the electrically conductive element 340 is shown. The cross section of the shaft of the electrically conductive element 340 is depicted as being circular but other cross-sectional shapes are also possible. As with the embodiments described above, in certain embodiments the electrically conductive element 340 may not include a shaft at all and may be substantially planar.

In the embodiment illustrated in FIG. 3D the electrically conductive element 340 includes a shaft which may be inserted into the clamp-like jaw 303 by forcing it between the first and second contact elements 304, 306 in the direction of arrow 342. Because of the flanged ends 323 of the first and second contact elements 304, 306 at the receiving end 313 of the clamp-like jaw 303, forcing the shaft of the electrically conductive element 342 into the clamp-like jaw 303 displaces the contact elements 304, 306 allowing the shaft of the electrically conductive element 340 into the clamp-like jaw 303. In other words, as the shaft of the electrically conductive element 340 is forced against the first and second contact elements 304, 306, the first contact element 304 is displaced upward and the second contact element 306 is displaced downward, according to the depicted orientation. Because the first and second contact elements 304, 306 are biased by the biasing element 344, the clamp-like jaw 303 widens and narrows depending on the position of the shaft of the electrically conductive element 340 within the clamp-like jaw 303.

Figure 3E:
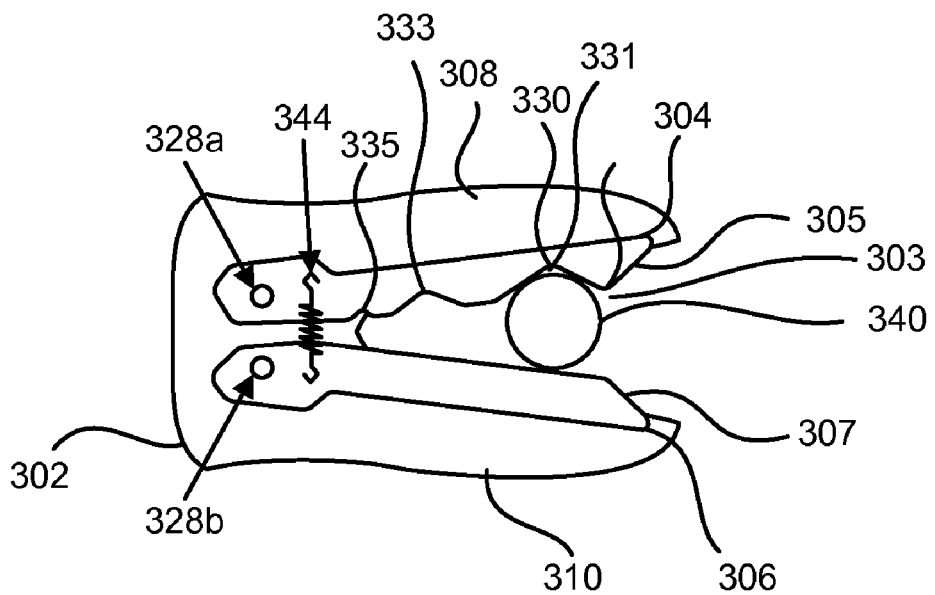
FIG. 3E is a cutaway side view of one embodiment of the apparatus of FIG. 2A engaging an electrically conductive element within a first stage in the scissor-like jaw.

Turning now to FIG. 3E, the shaft of the electrically conductive element 340 is shown after it has been inserted into the clamp-like jaw 303 of the apparatus 300 in the direction of the arrow 342 of FIG. 3D. The shaft of the electrically conductive element 340 is shown resting in a first stage 331 of the clamp-like jaw 303. The first stage 331 is formed between a valley 330 of the first contact element 304 and the second contact element 306. The valley 330, in conjunction with the biasing of the first and second contact elements 304, 306 towards a closed position help to maintain the shaft of the electrically conductive element 340 within the first stage 331. Similar to the clip 100 of FIGS. 1A-1J different ranges of shaft sizes may fit in the different stages 305. For example, a first range of shaft sizes may fit within the first stage 331, a second range of smaller shaft sizes may fit with the second stage 333, and a third range of still smaller shaft sizes may fit within the third stage 335.

Once again, the apparatus 300 is only exemplary and considerable variation, such as the variation mentioned in relation to FIGS. 1A-1J, is possible within the teaching of the present disclosure.

Figure 4:
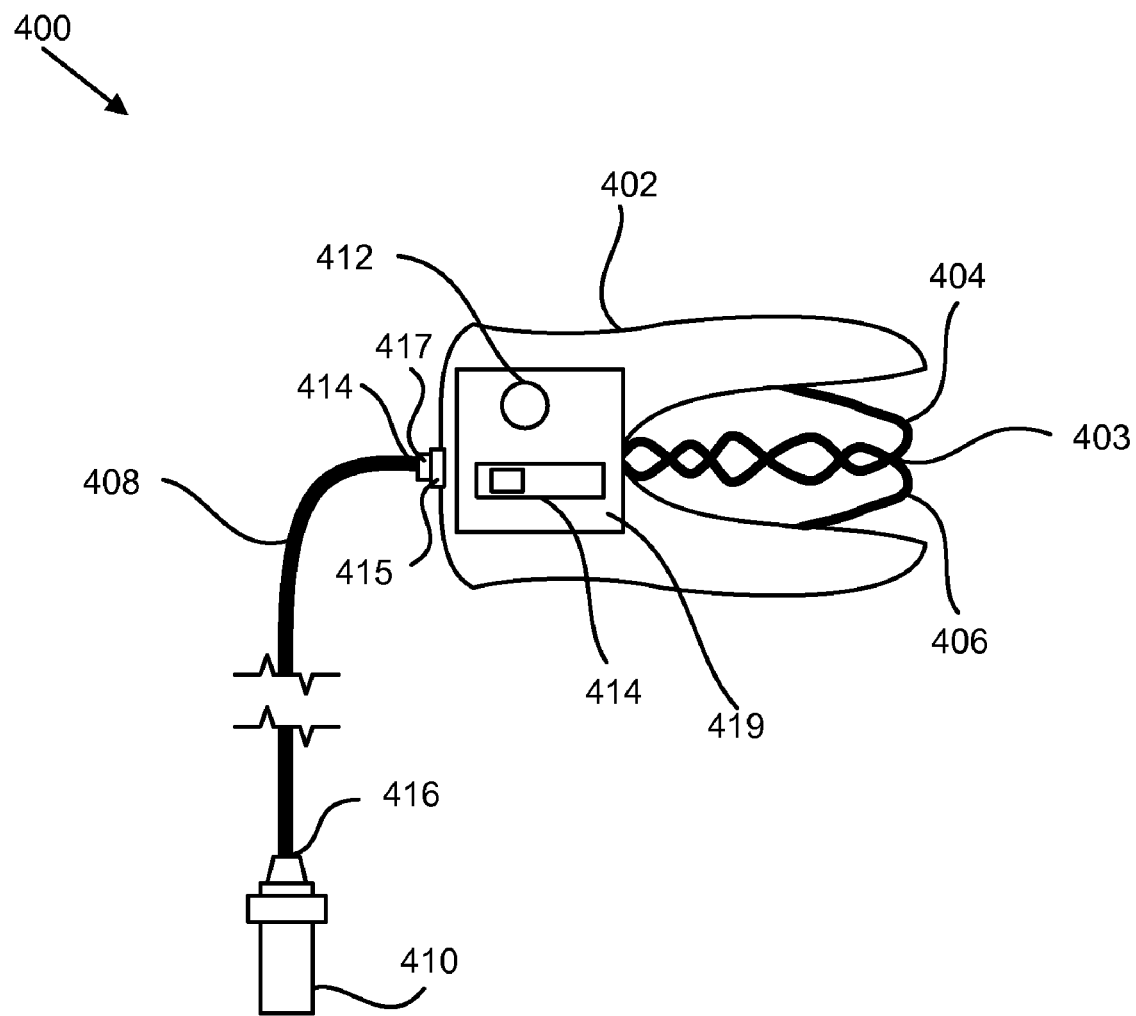
FIG. 4 is a side view illustrating one embodiment of an apparatus for creating an electrical connection with an electrically conductive element, the apparatus having an electrical cord, an indicator light, and a switch.

FIG. 4 is an additional embodiment of an apparatus 400 for creating an electrical connection with an electrically conductive element. The apparatus 400 is similar to the apparatus 100 of FIG. 1A-1J and includes additional structures and features. The apparatus 400 includes a housing 402 of similar structure to the housing 102 of FIGS. 1A-1J as well first and second contact elements 404, 406 substantially similar to the first and second contact elements 104, 106 of FIGS. 1A-1J. The apparatus 400 also includes a feedback indicator 412 that provides feedback to a user in response to a feedback signal from an electrically conductive element positioned within the scissor-like jaw 403. In certain embodiments the apparatus 400 may also include a switch 414 that operates to control the flow of an electrical current between a power source (not shown) and one or both of the first contact element 404 and the second contact element 406. The apparatus 400 may also include an electrical cord 408 extending into the housing 402 at a proximal end 414 and to a connector 410 at a distal end 416.

In certain embodiments at least one of the first contact element 404 and the second contact element 406 is coupled to an electrical connector 415. The electrical connector 415 maybe affixed to the housing 402 such that the housing 402 provides support for the electrical connector 415. The electrical connector 415 may operate to couple an electrical source (not shown) to at least one of the first and second contact elements 404, 406.

In one embodiment the housing 402 may be made of an electrically conductive material and at least one of the first contact element 404 or the second contact element 406 may be electrically coupled to the housing 402. In another embodiment the housing 402 may be made of a material that does not conduct electricity. In such an embodiment the housing may provide a structure that allows a user to grasp the apparatus 100 without the risk of electrical shock. In another embodiment each contact element 404, 406 may be electrically coupled to separate electrical sources. In yet another embodiment the housing 402 may include a ground wire.

In one embodiment the electrical connector 415 operates to receive a corresponding electrical connector 417 at the proximal end 414 of the electrical cord 408. In another embodiment, both the electrical connector 415 on the housing 402 and the corresponding electrical connector 417 of the electrical cord 408 may be omitted and the electrical cord 408 may be directly coupled to the first contact element 404, the second contact element 406, or both. In one embodiment the electrical cord 408 or the electrical connector 415 may be coupled to a switch 414 which may in turn be coupled to the first contact element 404, the second contact element 406, or both to control the flow of an electrical current between the electrical cord 408 and the first and second contact elements 404, 406. In another embodiment the feedback indicator 412 may be interposed between the electrical source (not shown) and the first contact element 404 and/or the second contact element 406 to provide feedback to a user as the user uses the apparatus 400.

In one embodiment the feedback indicator 412 may be coupled to only one of the first contact element 404 or the second contact element 406 and the electrical source (not shown) may be coupled to the other contact element 404, 406. In such an embodiment the feedback indicator 412 may indicate to a user when a circuit has been created between the first contact element 404 and the second contact element 406. One of skill in the art will recognize that the feedback indicator 412 may provide a user with other types of feedback depending on the type use of the apparatus 400.

The electrical cord 408, according to one embodiment, comprises one or more flexible conductors within an insulating material, similar to electrical cords well known in the art. The electrical cord 408 may be used to connect the apparatus 400 to an electrical source (not shown). The connector 410 is a connection mechanism to connect the electrical cord 408 to an electrical source and is only exemplary. The electrical source may be one of a variety of electrical sources such as a power supply, function generator, computer, or any other electrical source known in the art. The electrical connectors 410, 415, and 417 may correspond to one or more types of electrical sources or electrical coupling devices.

In certain embodiments one or more of the flexible conductors of the electrical cord 408 may be directly connected to one or both of the first and second contact elements 404, 406. Thus, when a connected electrical source applies a voltage to the apparatus 400, a voltage will also be applied to the first and second contact elements 404, 406 and any electrically conductive elements engaged in the scissor-like jaw 403.

The feedback indicator 412 may be used to indicate a certain condition or status to a user of the apparatus 400. For example, the apparatus 400 may be used to engage the shaft of an electrically conductive surgical tool for location of nerves. The feedback indicator 412 may receive a feedback signal from the electrically conductive surgical tool when a nerve is too close to a location at which the surgical tool is touching the body of a patient. In certain embodiments the feedback indicator 412 may be a simple indicator light. One of skill in the art will recognize that in other embodiments more complex feedback may be provided to the user by the feedback indicator 412. Using the feedback indicator 412 as a guide, a user, such as a surgeon or other medical staff, may be able to make decisions on where procedures or operations should be performed to avoid damaging nerves. Instead of being required to look at a computer screen or other device located away from the surgical procedure to determine the proximity of a nerve, the surgeon or medical staff can simply use a surgical tool, with an attached apparatus 400 having a feedback indicator 412 located near the surgical tool. The surgeon or medical staff, by paying attention to the feedback indicator 412, can determine where to make incisions, for example, or other take other steps necessary to perform a medical procedure.

According to one embodiment, feedback indicator 412 may be controlled by a computer or other device. For example, a computer may be connected to an EMG which senses the stimulation of nerves. The computer may be running software which decides when the feedback indicator 412 should be on or off. In such an embodiment, the computer or remote device may be connected to the apparatus 400 through the cord 408. For example, in addition to the conductor(s) within the cord 408 that supply a voltage to the first and second contact elements 404, 406, there may be an additional conductor that provides a signal to the feedback indicator 412 or other circuitry on or in the apparatus 400. The feedback indicator 412 may then be turned on or off based on the signal. In certain embodiments the feedback indicator 412 may be an audible feedback indicator such as a speaker or other sound producing device that provides feedback through an audible indicator.

In certain embodiments, wherein the feedback indicator 412 is a light, the light may change colors depending on the proximity of the surgical tool to the nerve. For example, the light may be colored yellow when the surgical tool is a certain predefined distance from a nerve indicating to the surgeon that it is safe to cautiously advance the surgical tool. As the surgical tool is advanced to a position that is closer to the nerve than the predefined distance the light may change from yellow to red indicating that the surgeon should stop advancing the surgical tool. In one embodiment, the light may be initially colored green indicating to the surgeon that the apparatus 400 is providing an electrical current to the surgical tool. A green light may also indicate that the surgical tool has not encountered a nerve. One of skill in the art will recognize that in certain embodiments the apparatus 400 may include more than one feedback indicators 412 rather than a single feedback indicator 412 configured to illuminate different colors.

The switch 414 allows a user to control the voltage applied to the first and second contact elements 404, 406. For example, according to one embodiment, the switch 414 comprises an open position and a closed position. When the switch 414 is placed in an open position an electrical connection between the contact elements 404, 406 and an electrical source is broken. When the switch 414 is placed in a closed position, an electrical connection between the contact elements 404, 406 and an electrical source is formed. Thus, using the switch 414 a user could selectively remove and apply a voltage to an electrically conductive element engaged by the first and second contact elements 404, 406.

According to another embodiment, the switch 414 may be a variable resistor, such as a potentiometer. In such an embodiment, in addition to having open and closed positions, the switch 414 has positions which provide varying levels of resistance. This allows the voltage level applied to the first and second contact elements 404, 406 to be manually controlled using the apparatus 400. This may be useful to limit over-stimulation of nerves or to reduce stimulation when a problem is encountered.

According to one embodiment, the feedback indicator 412 and the switch 414 may be mounted to a printed circuit board (PCB) 419 placed within the housing 402 of the apparatus 400. Wherein the feedback indicator 406 is a light, the light may be any type of light emitting device, such as a light emitting diode (LED). Additional circuitry may be found on the PCB 419, such as circuitry controlling the lighting of the feedback indicator 412. In one embodiment the feedback indicator 412 may be a red green combination LED and the PCB may be designed to change the color of the LED from green to amber to red or any variation in between depending on a feedback signal processed by the PCB.

The switch 414 is only exemplary and could be replaced by any other on off or switch or variable resistor. The switch 414 may be configured to control the amount or intensity of an electrical current delivered to the first and/or second contact element 404, 406. In certain embodiments the switch is electrically coupled to the PCB 419 and the PCB 419 provides circuitry to control the intensity of an electrical current delivered to the first and/or second contact element 404, 406.

Figure 5:
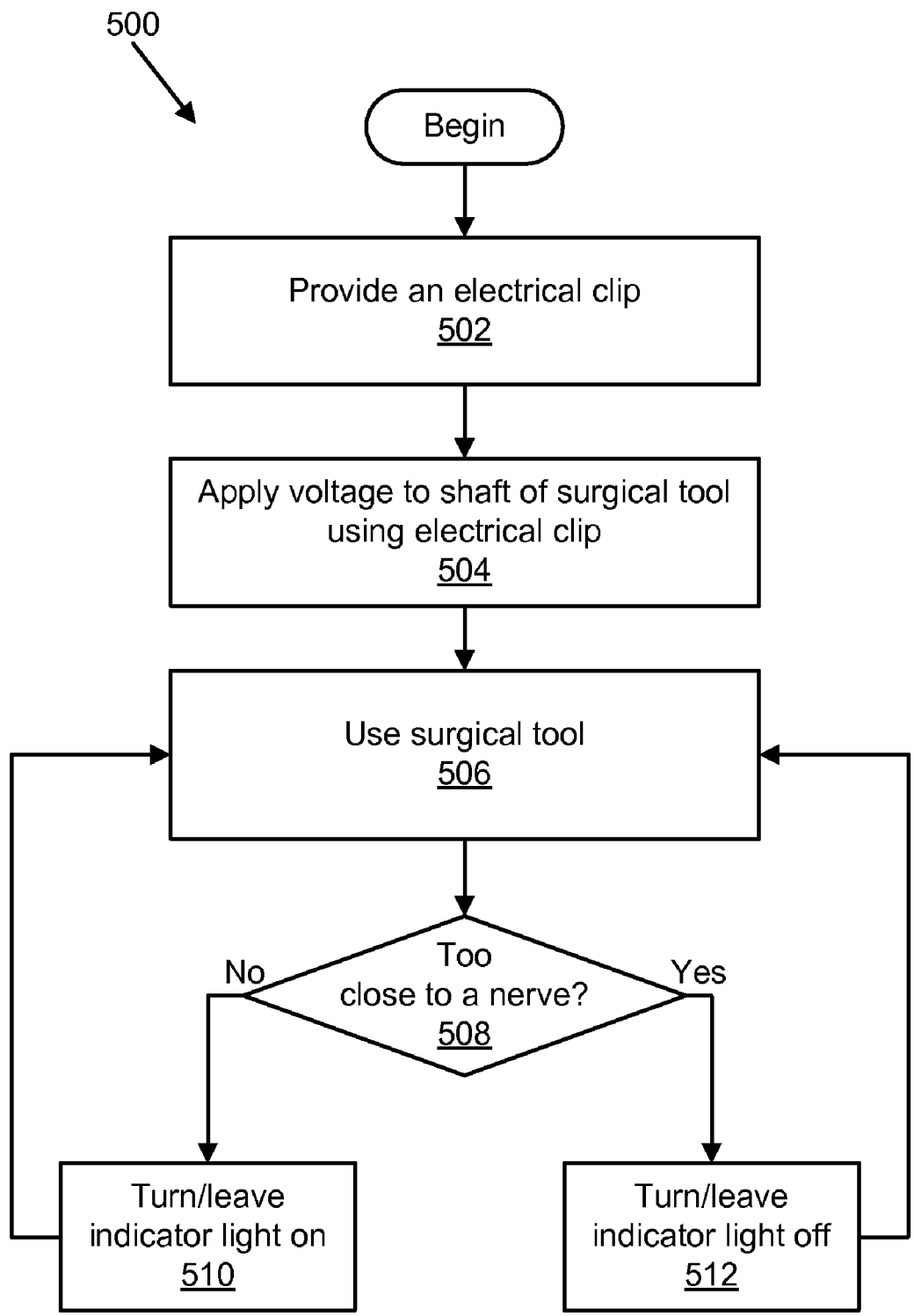
FIG. 5 is a schematic block diagram illustrating one embodiment of a method for using an apparatus for creating an electrical connection with an electrically conductive element.

FIG. 5 is a block diagram of a method 500 of using an electrical clip to locate nerves. The steps of the method 500 will be discussed in relation to the apparatus 400 of FIG. 4. However, as will be understood by one skilled in the art in light of the present disclosure, numerous other embodiments of electrical clips could be used in the method 500 with little or no variation.

The method begins by providing 502 an electrical clip such as apparatus 400. The apparatus 400 is used to apply 504 a voltage to the shaft of a surgical tool. This may be done by inserting the shaft of the surgical tool into the scissor-like jaw 403 of the apparatus 400 and applying a voltage to one of the first and second contact elements 404, 406. For example, the shaft may be inserted into the scissor-like jaw 403 in the manner previously discussed in relation to the apparatus 100, 200, 300, 400 of the previous figures. The voltage may be applied to the contact elements 404, 406, and thus to the shaft, using the connector 410 and cord 408. For example, the connector 410 may be connected to a computer, a power supply, a function generator, or other electrical source.

The surgical tool is then used 506 by a surgeon or other medical professional. The surgical tool may be used 506 by touching a portion of it to a location on a patient's body to see if a nerve is too close to that location, or the surgical tool may be used 506 according to a normal function. For example, a dilator may be used 506 for stretching an incision. Other surgical tools may be used 506 according to one their respective functions.

As the surgical tool is being used 506, a portion of it may be touched to a location on or within a patient's body. When the surgical tool is touching a patient's body too close to a nerve 508, the feedback indicator 412 is turned on 510. Otherwise, the feedback indicator 412 remains off 512. A computer or other device may be used in conjunction with an EMG to determine if, during use 506 of the surgical tool, the surgical tool is touching a location of the patient's body that is too close to a nerve. For example, the EMG may be used to monitor nerve stimulation of the patient. The EMG may be connected to the computer or other device having computer usable program code executable to perform operations for analyzing the signal or information provided by the EMG to determine if nerves have been stimulated to a certain level. If the nerves are determined to have been stimulated above a certain level, the computer or other device may determine that the tool is too close to a nerve 508. The computer or other device may then send a signal to the apparatus 400 to turn on 510 the feedback indicator 412. The surgical tool may continue to be used 506 until a surgeon or other medical staff is finished with the tool.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for creating an electrical connection with an electrically conductive element, the apparatus comprising:
   a first contact element having an engagement surface for engaging a first side of the electrically conductive element;
   a second contact element having an opposing engagement surface for engaging a second side of the electrically conductive element, the second contact element disposed opposite the first contact element, wherein the first contact element is slideable past the second contact element to form a scissor-like jaw;
   a plurality of stages formed in the scissor-like jaw, each stage comprising a valley formed in at least one of the engagement surface of the first contact element and the opposing engagement surface of the second contact element, each stage comprising a different sized stage; and
   wherein at least one of the first contact element and the second contact element comprise an electrically conductive material to conduct an electrical current between the electrically conductive element and at least one of the first contact element and the second contact element.

2. The apparatus of claim 1, wherein at least one of the first contact element and the second contact element comprise an angled section at a receiving end of the scissor-like jaw, wherein the angled section deflects to receive the electrically conductive element.

3. The apparatus of claim 1, wherein each stage comprises a successively smaller stage deeper within the scissor-like jaw.

4. The apparatus of claim 1, wherein the electrically conductive element is selectively placed in a different stage based on at least one of a size of the electrically conductive element and a desired amount of tension between the electrically conductive element and the first contact element and the second contact element.

5. The apparatus of claim 1, wherein the electrically conductive element comprises a shaft of a tool, wherein an electrical connection is maintained when the shaft of the tool is rotated relative to the scissor-like jaw.

6. The apparatus of claim 1, further comprising an electrical connector coupled to at least one of the first contact element and the second contact element.

7. The apparatus of claim 1, further comprising a feedback indicator that provides feedback to a user in response to a feedback signal from the electrically conductive element.

8. The apparatus of claim 1, further comprising at least one of a resistor, a potentiometer, and a switch for controlling a level of electric current between an electrical source and at least one of the one of the first contact element and the second contact element.

9. The apparatus of claim 1, wherein at least one of the first contact element and the second contact element is resiliently biased to position the scissor-like jaw in a closed position, wherein the first contact element overlaps the second contact element when the scissor-like jaw is positioned in the closed position.

10. The apparatus of claim 9, wherein at least one of the first contact element and the second contact element comprise a material having a structural resiliency sufficient to resiliently bias the scissor-like jaw in the closed position.

11. The apparatus of claim 9, wherein at least one of the first contact element and the second contact element comprise a wireform having a structural resiliency sufficient to resiliently bias the scissor-like jaw in the closed position.

12. The apparatus of claim 9, further comprising a biasing element coupled to at least one of the first contact element and the second contact element, wherein the biasing element resiliently biases the scissor-like jaw in the closed position.

13. The apparatus of claim 1, further comprising a housing that engages at least one of the first contact element and the second contact element to bias the scissor-like jaw in a closed position.

14. The apparatus of claim 13, wherein the housing comprises at least one prong rigidly extending from a substantially rigid support base, wherein the first contact element and the second contact element comprise a receiving end and a recessed end, wherein at least one of the first contact element and the second contact element is engaged with the housing at one or more of the receiving end and the recessed end.

15. The apparatus of claim 13, wherein the housing provides a substantially rigid support structure against which at least one of the first contact element and the second contact element apply a biasing force to bias the scissor-like jaw in the closed position.

16. An apparatus for creating an electrical connection with an electrically conductive element, the apparatus comprising:
   a first contact element having an engagement surface for engaging a first side of the electrically conductive element;
   a second contact element having an opposing engagement surface for engaging a second side of the electrically conductive element, the second contact element disposed opposite the first contact element, wherein the first contact element is slideable past the second contact element to form a scissor-like jaw;
   at least one stage formed in the scissor-like jaw, the at least one stage comprising a valley formed in at least one of the engagement surface of the first contact element and the opposing engagement surface of the second contact element;
   a housing that engages at least one of the first contact element and the second contact element to bias the scissor-like jaw in a closed position; and
   wherein at least one of the first contact element and the second contact element comprise an electrically conductive material to conduct an electrical current between the electrically conductive element and at least one of the first contact element and the second contact element.

17. The apparatus of claim 16, wherein the housing provides a substantially rigid support structure against which at least one of the first contact element and the second contact element apply a biasing force to bias the scissor-like jaw in the closed position, wherein at least one of the first contact element and the second contact element comprise a material having a structural resiliency sufficient to resiliently bias the scissor-like jaw in the closed position.

18. An apparatus for creating an electrical connection with an electrically conductive element, the apparatus comprising:
   a first contact element having an engagement surface for engaging a first side of the electrically conductive element;
   a second contact element having an opposing engagement surface for engaging a second side of the electrically conductive element, the second contact element disposed opposite the first contact element, wherein the first contact element is slideable past the second contact element to form a scissor-like jaw, wherein at least one of the first contact element and the second contact element is resiliently biased to position the scissor-like jaw in a closed position, the first contact element overlapping the second contact element when the scissor-like jaw is positioned in the closed position;
   at least one stage formed in the scissor-like jaw, the at least one stage comprising a valley formed in at least one of the engagement surface of the first contact element and the opposing engagement surface of the second contact element;
   a housing that engages at least one of the first contact element and the second contact element to bias the scissor-like jaw in the closed position, the housing comprising a substantially rigid support structure against which at least one of the first contact element and the second contact element apply a biasing force to bias the scissor-like jaw in the closed position;
   an electrical connector coupled to at least one of the first contact element and the second contact element; and
   wherein at least one of the first contact element and the second contact element comprise an electrically conductive material to conduct an electrical current between the electrically conductive element and at least one of the first contact element and the second contact element.

19. The apparatus of claim 18, wherein at least one of the first contact element and the second contact element comprise a wireform having a structural resiliency sufficient to resiliently bias the scissor-like jaw in the closed position.

* * * * *